(12) United States Patent
Thomson et al.

(10) Patent No.: US 12,421,490 B2
(45) Date of Patent: Sep. 23, 2025

(54) AGROBACTERIUM TUMEFACIENS STRAIN AND DERIVATIVES THEREOF

(71) Applicant: The United States of America, as represented by The Secretary of Agriculture, Washington, DC (US)

(72) Inventors: James G. Thomson, El Cerrito, CA (US); Diaa F. Alabed, Sacramento, CA (US)

(73) Assignee: The United States of America, as represented by The Secretary of Agriculture, Washingto, DC (US)

( * ) Notice: Subject to any disclaimer, the term of this patent is extended or adjusted under 35 U.S.C. 154(b) by 188 days.

(21) Appl. No.: 18/295,882

(22) Filed: Apr. 5, 2023

(65) Prior Publication Data

US 2023/0399603 A1    Dec. 14, 2023

Related U.S. Application Data

(60) Provisional application No. 63/350,930, filed on Jun. 10, 2022.

(51) Int. Cl.
*C12N 1/20* (2006.01)
*A01H 6/78* (2018.01)
*C12N 15/82* (2006.01)

(52) U.S. Cl.
CPC .......... *C12N 1/205* (2021.05); *A01H 6/785* (2018.05); *C12N 15/8205* (2013.01)

(58) Field of Classification Search
None
See application file for complete search history.

(56) References Cited

PUBLICATIONS

Dutt, M., and J. W. Grosser. "Evaluation of parameters affecting Agrobacterium-mediated transformation of citrus." Plant Cell, Tissue and Organ Culture (PCTOC) 98 (2009): 331-340. (Year: 2009).*
DE Akiyoshi, et al., 1985, "Cloning and nucleotide sequence of the tzs gene from Agrobacterium tumefaciens strain T37," Nucleic Acids Res. 13: 2773-2788.
D Alabed, et al., 2019, "Draft Genome Sequence of *Serratia* sp. 1D1416," Microbiol. Resour. Announc. 8(3) e01354.
RF Barker, et al., 1983, "Nucleotide sequence of the T-DNA region from the Agrobacterium tumefaciens octopine Ti plasmid pTi15995," Plant Mol. Biol. 2: 335-350.

JS Beaty, et al., 1986, "Tzs, a nopaline Ti plasmid gene from Agrobacterium tumefaciens associated with trans-zeatin biosynthesis," Mol. Gen. Genet. 203: 274-280.
M Cheng et al., 2004, "Invited Review: Factors influencing Agrobacterium-mediated transformation of monocotyledonous species," In Vitro Cell. Dev. Biol.-Plant 40: 31-45.
R Collier et al., 2018, "A versatile and robust Agrobacterium-based gene stacking system generates high-quality transgenic *Arabidopsis* plants," Plant J. 95: 573-583.
JA Driver and AH Kuniyuki, 1984, "In Vitro Propagation of Paradox Walnut Rootstock," HortScience 19(4): 507-509.
B Goodner, et al., 2001, "Genome Sequence of the Plant Pathogen and Biotechnology Agent Agrobacterium tumefaciens C58," Science 294 (5550): 2323-2328.
LT Hathwaik, et al., 2021, "Gene Assembly in Agrobacterium via Nucleic Acid Transfer Using Recombinase Technology (GAANTRY)," in Anindya Bandyopadhyay and Roger Thilmony (eds.), Rice Genome Engineering and Gene Editing: Methods and Protocols, Methods in Molecular Biology, vol. 2238, https://doi.org/10.1007/978-1-0716-1068-8_1,@ Springer Science+Business Media, LLC, part of Springer Nature.
EE Hood, et al., 1993, "New Agrobacterium helper plasmids for gene transfer to plants," Transgenic Res. 2: 208-218.
HH Hwang et al., 2013, "Characterization and host range of five tumorigenic Agrobacterium tumefaciens strains and possible application in plant transient transformation assays," Plant Pat. 62: 1384-1397.
MV Matz, et al., 1999, "Fluorescent Proteins from Nonbioluminescent *Anthozoa* Species," Nat. Biotechnol. 17: 969-973.
KF McCue, et al., 2019, "Transgene stacking in potato using the GAANTRY system," BMC Res. Notes 12: 457.
GK Powell, et al., 1988, "Inducible expression of cytokinin biosynthesis in Agrobacterium tumefaciens by plant phenolics," Mol. Plant Microbe Interact. 1: 235-242.
SD Rodrigues, et al., 2020, "Efficient CRISPR-mediated base editing in *Agrobacterium* spp," Proc. Natl. Acad. Sci. U.S.A. 118(2): e2013338118.
D Sciaky, et al., 1978, "Fingerprints of Agrobacterium Ti plasmids," Plasmid 1: 238-253.
DW Wood, et al., 2001, "The Genome of the Natural Genetic Engineer Agrobacterium tumefaciens C58," Science 294 (5550): 2317-2323.
Y-Y Zhang, et al., 2017, "A simple and efficient in planta transformation method for pommelo (*Citurs maxima*) using Agrobacterium tumefaciens," Sci. Hortic. 214: 174-179.

* cited by examiner

*Primary Examiner* — Charles Logsdon
(74) *Attorney, Agent, or Firm* — John Fado; Maria Restrepo-Hartwig

(57) ABSTRACT

The disclosure relates to novel disarmed *Agrobacterium tumefaciens* strains, uses of these disarmed *Agrobacterium* strains, and kits comprising such disarmed *Agrobacterium* strains. The disarmed *Agrobacterium* strains are effective for the transformation of plant, fungal, or algae cells. The *Agrobacterium* strains are very effective for the transformation of citrus plant cells.

18 Claims, 18 Drawing Sheets

Specification includes a Sequence Listing.

SEQUENCE LISTING

```
Sequence total quantity: 24
SEQ ID NO: 1                  moltype = DNA   length = 24
FEATURE                       Location/Qualifiers
source                        1..24
                              mol_type = other DNA
                              organism = synthetic construct
SEQUENCE: 1
gattgaacaa gatggattgc acgc                                         24

SEQ ID NO: 2                  moltype = DNA   length = 25
FEATURE                       Location/Qualifiers
source                        1..25
                              mol_type = other DNA
                              organism = synthetic construct
SEQUENCE: 2
ccacagtcga tgaatccaga aaagc                                        25

SEQ ID NO: 3                  moltype = DNA   length = 30
FEATURE                       Location/Qualifiers
source                        1..30
                              mol_type = other DNA
                              organism = synthetic construct
SEQUENCE: 3
gctctgaacg atcattgagg agtctcgagc                                   30

SEQ ID NO: 4                  moltype = DNA   length = 31
FEATURE                       Location/Qualifiers
source                        1..31
                              mol_type = other DNA
                              organism = synthetic construct
SEQUENCE: 4
gtgccaagtt atcaatggag aaccagaaca c                                 31

SEQ ID NO: 5                  moltype = DNA   length = 30
FEATURE                       Location/Qualifiers
source                        1..30
                              mol_type = other DNA
                              organism = synthetic construct
SEQUENCE: 5
ggttcaaacac atcttcaggt ataaggctcc                                  30

SEQ ID NO: 6                  moltype = DNA   length = 33
FEATURE                       Location/Qualifiers
source                        1..33
                              mol_type = other DNA
                              organism = synthetic construct
SEQUENCE: 6
cgaagtatcc catcatcaga aacgatcaaa cac                               33

SEQ ID NO: 7                  moltype = DNA   length = 20
FEATURE                       Location/Qualifiers
source                        1..20
                              mol_type = other DNA
                              organism = synthetic construct
SEQUENCE: 7
cgtgttggaa cggtcttgcc                                              20

SEQ ID NO: 8                  moltype = DNA   length = 31
FEATURE                       Location/Qualifiers
source                        1..31
                              mol_type = other DNA
                              organism = synthetic construct
SEQUENCE: 8
cagactttgc tcatgttacc gatgctattc g                                 31

SEQ ID NO: 9                  moltype = DNA   length = 26
FEATURE                       Location/Qualifiers
source                        1..26
                              mol_type = other DNA
                              organism = synthetic construct
SEQUENCE: 9
cgattttaac ctcggtcgga gactgg                                       26

SEQ ID NO: 10                 moltype = DNA   length = 27
FEATURE                       Location/Qualifiers
source                        1..27
                              mol_type = other DNA
                              organism = synthetic construct
```

```
SEQUENCE: 10
ccatttattc agcatcggct tggaacg                                                27

SEQ ID NO: 11            moltype = DNA   length = 26
FEATURE                  Location/Qualifiers
source                   1..26
                         mol_type = other DNA
                         organism = synthetic construct
SEQUENCE: 11
ggatcctcgg ggccaaactc ctcaat                                                 26

SEQ ID NO: 12            moltype = DNA   length = 26
FEATURE                  Location/Qualifiers
source                   1..26
                         mol_type = other DNA
                         organism = synthetic construct
SEQUENCE: 12
ggatccgatg gccatccaac acgcag                                                 26

SEQ ID NO: 13            moltype = DNA   length = 20
FEATURE                  Location/Qualifiers
source                   1..20
                         mol_type = other DNA
                         organism = synthetic construct
SEQUENCE: 13
attcaagaat gcaccgcgag                                                        20

SEQ ID NO: 14            moltype = DNA   length = 21
FEATURE                  Location/Qualifiers
source                   1..21
                         mol_type = other DNA
                         organism = synthetic construct
SEQUENCE: 14
tatattaaga tccaagtgtg g                                                      21

SEQ ID NO: 15            moltype = DNA   length = 26
FEATURE                  Location/Qualifiers
source                   1..26
                         mol_type = other DNA
                         organism = synthetic construct
SEQUENCE: 15
cgattttaac ctcggtcgga gactgg                                                 26

SEQ ID NO: 16            moltype = DNA   length = 27
FEATURE                  Location/Qualifiers
source                   1..27
                         mol_type = other DNA
                         organism = synthetic construct
SEQUENCE: 16
ccatttattc agcatcggct tggaacg                                                27

SEQ ID NO: 17            moltype = DNA   length = 27
FEATURE                  Location/Qualifiers
source                   1..27
                         mol_type = other DNA
                         organism = synthetic construct
SEQUENCE: 17
cgattttatt gccaagcctt ttgggac                                                27

SEQ ID NO: 18            moltype = DNA   length = 16
FEATURE                  Location/Qualifiers
source                   1..16
                         mol_type = other DNA
                         organism = synthetic construct
SEQUENCE: 18
ccgccatcac accccc                                                            16

SEQ ID NO: 19            moltype = DNA   length = 16
FEATURE                  Location/Qualifiers
source                   1..16
                         mol_type = other DNA
                         organism = synthetic construct
SEQUENCE: 19
atggctaaag tggcaa                                                            16

SEQ ID NO: 20            moltype = DNA   length = 20
FEATURE                  Location/Qualifiers
source                   1..20
                         mol_type = other DNA
```

```
                          organism = synthetic construct
SEQUENCE: 20
tcaaactcca ttgagagccc                                                    20

SEQ ID NO: 21             moltype = DNA  length = 25
FEATURE                   Location/Qualifiers
source                    1..25
                          mol_type = other DNA
                          organism = synthetic construct
SEQUENCE: 21
gccatcatgc cgttcaaagt gcagg                                              25

SEQ ID NO: 22             moltype = DNA  length = 32
FEATURE                   Location/Qualifiers
source                    1..32
                          mol_type = other DNA
                          organism = synthetic construct
SEQUENCE: 22
cggcgttaat tcagtacatt aaaaacgtcc gc                                      32

SEQ ID NO: 23             moltype = DNA  length = 94
FEATURE                   Location/Qualifiers
source                    1..94
                          mol_type = other DNA
                          organism = synthetic construct
SEQUENCE: 23
gatggcacaa aattctttgc gtctcgtaga ggataaatcg gtggataaaa gcaaggcact        60
ggaagcggcg ctctcccaga tcgaacggtc gttc                                    94

SEQ ID NO: 24             moltype = AA  length = 31
FEATURE                   Location/Qualifiers
source                    1..31
                          mol_type = protein
                          organism = synthetic construct
SEQUENCE: 24
MAQNSLRLVE DKSVDKSKAL EAALSQIERS F                                       31
```

AGROBACTERIUM TUMEFACIENS STRAIN AND DERIVATIVES THEREOF

CROSS-REFERENCE TO RELATED APPLICATIONS

This application claims the benefit of U.S. Provisional Application No. 63/350,930 filed Jun. 10, 2022. The content of this provisional patent application is hereby expressly incorporated by reference in its entirety.

FIELD OF THE INVENTION

The disclosure relates generally to the field of plant biotechnology. More specifically, the disclosure relates to Agrobacterium strains and cells which have been modified to be useful for transformation of host cells, such as plants, algae, and fungi. Methods of using such modified *Agrobacterium* strains, and plants produced with such *Agrobacterium* strains are also disclosed.

SEQUENCE LISTING

The instant application contains a Sequence Listing XML required by 37 C.F.R. § 1.831(a) which has been submitted in XML file format via the USPTO patent electronic filing system, and is hereby incorporated by reference in its entirety. The XML file was created on Apr. 3, 2023, is named Sequence Listing CONVERSION-0027.21.XML, and has 21.7 KB.

BACKGROUND OF THE INVENTION

*Agrobacterium tumefaciens* is a gram-negative soil bacteria that causes the crown gall disease in plants by infecting cells through wound sites. *A. tumefaciens* infects by injecting into the cell a strand of DNA (T-DNA) derived from the large tumor-inducing (Ti) plasmid. The T-DNA then integrates into a chromosomal location in the plant and produces enzymes that synthesize hormones which cause the crown gall symptoms, including tumor formation. The genes encoding these enzymes, and the eukaryotic regulatory control elements associated therewith, are located on the T-DNA. In addition, the integrated T-DNA also encodes enzymes that direct the synthesis of compounds known as opines, which are amino acid and sugar derivatives. Exactly which opines are produced varies depending upon the *A. tumefaciens* strain.

Mobilization of the T-DNA requires proteins encoded by the vir genes, which are genes located elsewhere on the Ti plasmid and on the bacterial chromosome. The vir genes are activated by certain elicitors from wounded plant cells and act within the *A. tumefaciens* cell to synthesize and transfer a single-stranded copy of the T-DNA to the plant cell. The T-DNA sequence on the Ti plasmid is flanked by short 24-bp imperfect direct repeats, which are required for the recognition of the T-DNA. Sequences immediately surrounding these borders appear to be involved in the polarity of single stranded T-DNA synthesis, which initiates at the right border.

The discovery of the mechanism by which *A. tumefaciens* infects plant cells, i.e. by DNA transfer, led to the realization that this microorganism might be useful, via its Ti plasmid, for transferring agronomically useful genes to plants. It is known in the art that foreign DNA flanked by T-DNA border sequences can be transferred into plant cells using *A. tumefaciens* as the vector. Furthermore, inactivation or removal of the native T-DNA genes involved in hormone synthesis renders *A. tumefaciens* incapable of producing the crown gall disease symptoms. This process of inactivating or removing genes responsible for disease symptoms is termed "disarming." Disarmed *Agrobacterium* strains are now routinely used to introduce exogenous DNA into plants by a process referred to as *Agrobacterium*-mediated transformation.

*Agrobacterium* has a diverse dicot host range, and additionally some monocot families. There are several different strains of *Agrobacterium*. A major disadvantage of using *Agrobacterium* for plant transformation is the organism's host specificity, resulting in low levels of transformation in certain plant species and/or genotypes. *Citrus* plants have proven to be very difficult to transform with *Agrobacterium*. This is at least in part because citrus is refractory to infection by known strains of *A. tumefaciens*. Studies with different *Agrobacterium* strains have suggested that citrus plant susceptibility to *Agrobacterium* is limited, and may be dependent on both, the cultivar and the bacterial strain. One strain, C58 with a nopaline-type chromosomal background, but containing the Ti plasmid, pTiBo542 from A281 is a supervirulent, broad host-range, L,L-succinamopine-type *A. tumefaciens* was produced. Disarming this strain has produced EHA101 and EHA105, strains now widely used in conjunction with soybean transformation.

Transformation of juvenile citrus using *Agrobacterium* has been hampered by low transformation efficiencies. Transformation of commercial varieties of mature citrus using *Agrobacterium* is so rare as to be practically useless. Transfer of DNA to citrus cells by non-*Agrobacterium* bacterial strains has not been reported. There is, therefore, a great need in the art for the development of improved methods allowing the transformation of commercially-important citrus crop varieties using any means, and improving transformation efficiencies of mature citrus and citrus in general. Thus, there is still a significant need for strains of *Agrobacterium* capable of effectively and efficiently transforming citrus plants.

Use of symbionts to modify a plant characteristic without modifying the plant genome is disclosed in international patent publication No. WO 2021/055,656.

SUMMARY OF THE INVENTION

Provided herein is a disarmed *Agrobacterium* strain and derivatives thereof that efficiently transform citrus plants. The disclosure also provides compositions comprising such disarmed strains, kits comprising such disarmed strains or compositions, and methods of using such disarmed strains and/or compositions to transform citrus plants/tissue.

The disclosure relates to disarmed *Agrobacterium* strain 1416G having ATCC deposit No. PTA-127288, and derivatives thereof. In some embodiments of the disclosure, the disarmed *Agrobacterium* strain comprises a 145 bp non-coding terminator sequence for the tomato pectinase open reading frame (TermA2). In some embodiments of the disclosure, the disarmed *Agrobacterium* strain comprises a 55 bp attB (TP901) site and a 789 bp Gentamicin 3 acetyltransferase gene. In some embodiments of the disclosure, the disarmed *Agrobacterium* strain comprises 789 bp from Gentamicin 3 acetyltransferase gene (aacC1). In some embodiments of the disclosure, the disarmed *Agrobacterium* strain comprises a 54 bp A118 phage attachment site (A118 attP). In some embodiments of the disclosure, the disarmed *Agrobacterium* strain comprises a 106 bp ParA resolution site. In some embodiments of the disclosure the disarmed *Agrobacterium* strain is *Agrobacterium* strain 1416G-NRB3 or *Agrobacterium* strain 1416Gr.

In an embodiment, the disclosure relates to a transgenic plant, plant tissue, plant cell, algae, or fungi having a polynucleotide of interest produced with the disarmed *Agrobacterium* strain 1416G having ATCC deposit No. PTA-127288 or a derivative thereof having the polynucleotide of interest. In some embodiments of the disclosure the transgenic plant, plant tissue, or plant cell produced with a disarmed *Agrobacterium* strain of the disclosure is derived from a citrus plant or part thereof. In some embodiments of the disclosure the citrus plant or part thereof transformed with a disarmed *Agrobacterium* strain of the disclosure is from a lime, a lemon, an orange, a citron, or a grapefruit.

In an embodiment, the disclosure relates to a method for producing a transgenic plant, fungal, or algae cell having a polynucleotide of interest. The method comprises contacting the plant, fungal, or algae cell with a culture comprising a disarmed *Agrobacterium* of the disclosure having a polynucleotide of interest, and incubating the plant, fungal, or algae cell in contact with the disarmed *Agrobacterium* strain having the polynucleotide of interest in selection regeneration media at a proper temperature and for a sufficient amount of time to allow for the formation of a transgenic plant, fungal, or algae cell. In some embodiments of the disclosure,

BRIEF DESCRIPTION OF THE DRAWINGS

FIG. 2A shows germinated CrZ seedlings; FIG. 2B shows transformed explants cultured on kanamycin selection media; FIG. 2C shows proliferated cells on the transformed cut side of the epicotyl; FIG. 2D and FIG. 2E show DsRed expression in proliferated cells; FIG. 2F shows shoot regeneration on selection media; FIG. 2G shows a putative regenerated shoot; FIG. 2H shows uniform DsRed expression on a transgenic shoot; and FIG. 2I shows shoot elongation and rooting of transgenic CrZ shoots.

FIG. 3A shows DsRed expression of an explant transformed with 1104; FIG. 3B shows DsRed expression of an explant transformed with 159; FIG. 3C shows DsRed expression of an explant transformed with 1526; FIG. 3D shows DsRed expression of an explant transformed with 1416; FIG. 3E shows DsRed expression of an explant transformed with 1565; and FIG. 3F shows DsRed expression of an explant transformed with EHA105 (positive control).

FIG. 5A presents an image of healthy tissues transformed with disarmed strain EHA105; FIG. 5B presents an image of proliferating tissues transformed with disarmed strain EHA105; FIG. 5C presents an image of healthy tissues transformed with wildtype 1416; FIG. 5D presents an image of proliferating tissues transformed with wildtype 1416; FIG. 5E presents an image of healthy tissues transformed with wildtype 1104; FIG. 5F presents an images of bacterial overgrowth, and necrotic and dying tissues transformed with wildtype 1104. FIG. 5A; FIG. 5C; and FIG. 5E present images of regenerating shoots in petri dishes. FIG. 5B; FIG. 5D; and FIG. 5F present higher magnification images of the transformed tissues.

FIG. 7A presents an image of tumors formed when transformed with wildtype strain 1416; FIG. 7B presents an image of the DsRed expression in tissues transformed with wildtype strain 1416; FIG. 7C presents an image of tumors formed when transformed with wild type strain 159; FIG. 7D presents an image of the DsRed expression in tissues transformed with wildtype strain 159.

FIG. 8A shows light microscopy images of directly regenerated shoots; FIG. 8B shows light microscopy images of normal transgenic regenerated shoots on SMM. FIG. 8C shows DsRed fluorescent filter images of directly regenerated shoots; FIG. 8B shows DsRed fluorescent filter images of normal transgenic regenerated shoots on Shooting Media.

FIG. 9A shows images of wild type shoots cultured on regeneration media; FIG. 9B shows images of shoots transformed with wild type strain 1416; FIG. 9C shows images of shoots transformed with EHA105; FIG. 9D shows stable DsRed expression in shoots regenerated from wild type strain 1416.

FIG. 11A shows a petri dish with small shoots; FIG. 11B shows larger shoots in the Rooting media.

FIG. 13A shows an image of a sterilized mature transformed Mexican lime shoot; FIG. 13B shows an image of the stable DsRed expression in the sterilized mature transformed Mexican lime shoot;

FIG. 13C shows an image of a sterilized mature transformed Naval orange; FIG. 13D shows an image of the stable DsRed expression in the sterilized mature transformed Naval orange; FIG. 13E shows an image of a sterilized mature transformed clementine; FIG. 13F shows an image of the stable DsRed expression in the sterilized mature transformed clementine; FIG. 13G shows an image of a sterilized mature transformed lemon; FIG. 13F shows an image of the stable DsRed expression in the sterilized mature transformed lemon.

FIG. 14A shows a light microscope image of tumors in transformed clementine; FIG. 14B shows a fluorescent image of the same clementine section; FIG. 14C shows a fluorescent image of a different clementine section expressing DsRed; FIG. 14D shows a fluorescent image of a transformed clementine tissue not expressing DsRed; FIG. 14E shows a light microscope image of a gall in transformed lemon; FIG. 14F shows a fluorescent image of the same lemon section expressing DsRed; FIG. 14G shows a light microscope image of galls formed on a transformed lemon; FIG. 14H shows a fluorescent image of the same galls expressing DsRed.

FIG. 16A shows an image of a transformed Lisbon lemon 8A; FIG. 16B shows an image of a transformed Washington naval orange; FIG. 16C shows an image of a transformed Mexican lime; and FIG. 16D shows an image of a transformed grapefruit.

BRIEF DESCRIPTION OF THE SEQUENCE LISTING

Figure 1:
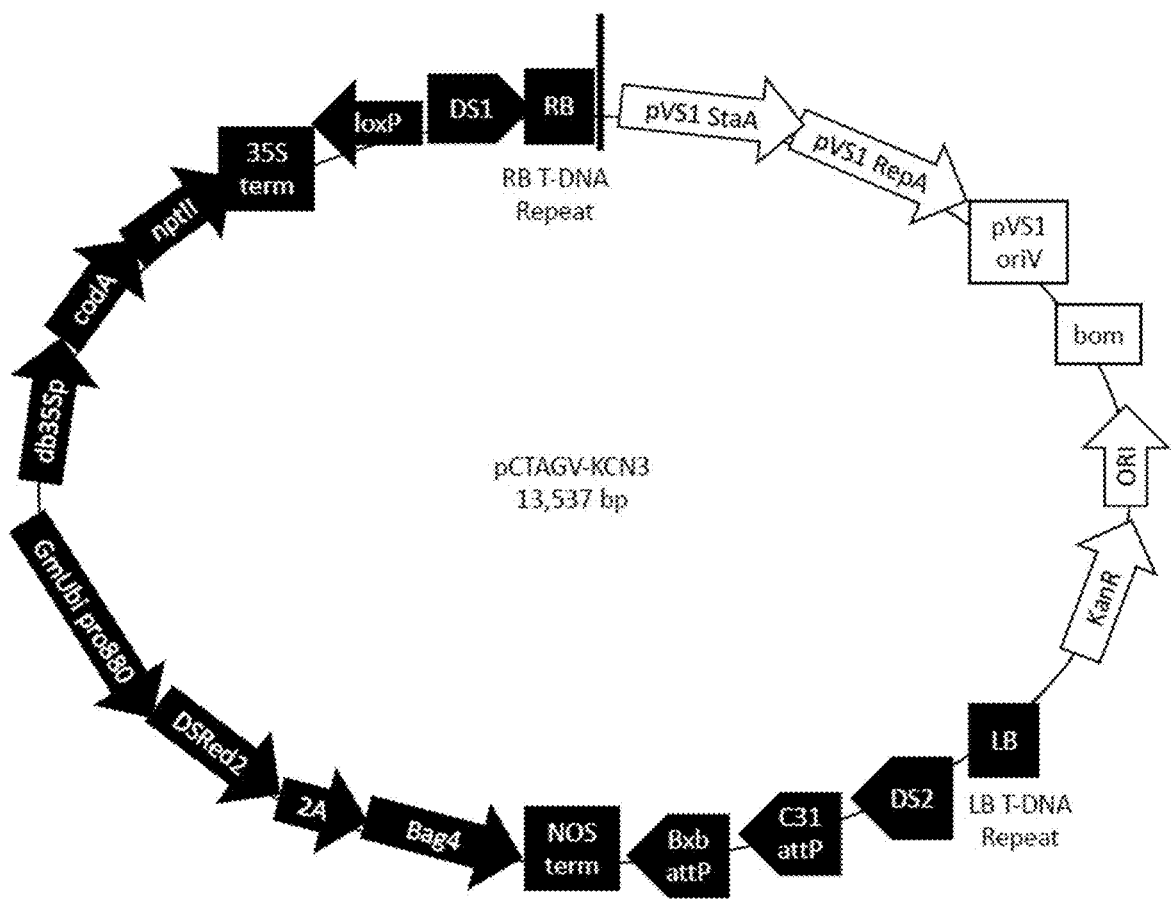
FIG. 1 depicts a map of the binary vector pCTAGV-KCN3. Starting at the 12 o'clock position and in a clockwise orientation, the pCTAGV-KCN3 vector contains DNA sequences corresponding to the stability protein from the plasmid pVS1 (pVS1 StaA); the replication protein from plasmid pVS1 (pVS1 RepA); the basis of mobility site (bom); an origin of replication (ori)*; a kanamycin resistance gene (KanR)*; an *Agrobacterium* left border T-DNA repeat (LB T-DNA repeat); a dissociation element 2 (DS element 2); an attP(phiC31) site (C31 attP); an attP(Bxb1) site (Bxb1 attP); a termination signal (Term)*; a NOS terminator (Nos Term); the BAG4 anti apoptosis gene (BAG4m)*; a 2A self-cleaving peptide (2A); marker gene DsRed (DSred)* under the control of GmUbi3 promoter with intron (GmUbi3 promoter 880)*; double CaMV35S promoter (db35S); a fusion of selectable marker genes codA and nptII (CodA::NPTII); a CaMV35S poly A terminator (35S Term); a loxP(Cre) site (loxP); a dissociation element 1 (DS element 1); and the *Agrobacterium* right border T-DNA repeat (RB T-DNA repeat). Sequences indicated with an asterisk are in a different orientation than the remaining sequences.

The nucleotide sequences disclosed in the specification are listed in Table 1, below

TABLE 1

SEQUENCES

| SEQ ID NO | Type | Description | Sequence |
|---|---|---|---|
| 1 | DNA | NptII forward | GATTGAACAAGATGGATTGCA CGC |
| 2 | DNA | NptII reverse | CCACAGTCGATGAATCCAGAA AAGC |
| 3 | DNA | CPro forward | GCTCTGAACGATCATTGAGGA GTCTCGAGC |
| 4 | DNA | CPro reverse | GTGCCAAGTTATCAATGGAGA ACCAGAACAC |
| 5 | DNA | Lod forward | GGTTCAACACATCTTCAGGTA TAAGGCTCC |
| 6 | DNA | Lod reverse | CGAAGTATCCCATCATCAGAA ACGATCAAACAC |
| 7 | DNA | GpDp forward | CGTGTTGGAACGGTCTTGCC |
| 9 | DNA | NNond forward | CGATTTTAACCTCGGTCGGA GACTGG |
| 10 | DNA | NNond reverse | CCATTTATTCAGCATCGGC TTGGAACG |
| 11 | DNA | Tzs forward | GGATCCTCGGGGCCAAACT CCTCAAT |
| 12 | DNA | Tzs reverse | GGATCCGATGGCCATCCAA CACGCAG |

TABLE 1-continued

SEQUENCES

| SEQ ID NO | Type | Description | Sequence |
|---|---|---|---|
| 13 | DNA | Acs forward | ATTCAAGAATGCACCGCGAG |
| 14 | DNA | Acs reverse | TATATTAAGATCCAAGTGTGG |
| 15 | DNA | Nos forward | CGATTTTAACCTCGGTCGGAGACTGG |
| 16 | DNA | Nos reverse | CCATTTATTCAGCATCGGCTTGGAACG |
| 17 | DNA | Vir G forward | CGATTTTATTGCCAAGCCTTTTGGGAC |
| 18 | DNA | Vir G reverse | CCGCCATCACACCCCC |
| 19 | DNA | Ocs forward | ATGGCTAAAGTGGCAA |
| 20 | DNA | Ocs reverse | TCAAACTCCATTGAGAGCCC |
| 21 | DNA | Aph3 forward | GCCATCATGCCGTTCAAAGTGCAGG |
| 22 | DNA | Aph3 reverse | CGGCGTTAATTCAGTACATTAAAAACGTCCGC |
| 23 | DNA | 1416Gr rec A | GATGGCACAAAATTCTTTGCGTCTCGTAGAGGATAAATCGGTGGATAAAAGCAAGGCACTGGAAGCGGCGCTCTCCCAGATCGAACGGTCGTTC |
| 24 | AA | 1416Gr rec A | MAQNSLRLVEDKSVDKSKALEAALSQIERSF |

Deposit Under Terms of Budapest Treaty

The inventors have deposited samples of the disarmed 1416G *Agrobacterium* strain with the American Type Culture Collection (ATCC). ATCC is located at 10801 University Boulevard, Manassas, Virginia, USA 201102204. All restrictions on the availability to the public of the deposited biological material identified herein will be irrevocably removed upon the granting of a patent.

The material was deposited on 19 May 2022, and received ATCC Accession No. PTA-127288. The biological materials identified herein have been deposited under conditions such that access to the microorganisms are available during the pendency of the patent application to one determined by the Commissioner to be entitled thereto under 37 C.F.R. § 1.14 and 35 U.S.C § 122.

The deposited biological material will be maintained with all the care necessary to keep it viable and uncontaminated for a period of at least five years after the most recent request for the furnishing of a sample of the deposited microorganism, and in any case, for a period of at least thirty (30) years after the date of deposit for the enforceable life of the patent, whichever period is longer.

DETAILED DESCRIPTION

The present disclosure relates generally to the field of plant biotechnology. More specifically, the disclosure relates to *Agrobacterium* strains and cells which have been modified to be useful for transformation of host cells, such as plants, algae and fungi, methods of using such modified *Agrobacterium* strains, and transgenic organisms produced with such *Agrobacterium* strains.

The following definitions will aid in the understanding of the description of the disclosure.

The term "*Agrobacterium*" as used herein refers to a soil-borne, Gram-negative, rod-shaped phytopathogenic bacterium. The cells are normally rod-shaped (0.6-1.0 µm by 1.5-3.0 µm), occur singly or in pairs, without endospore, and are motile by one to six peritrichous flagella. Considerable extracellular polysaccharide slime is usually produced during growth on carbohydrate-containing media. The species of *Agrobacterium*, *A. tumefaciens* (syn. *A. radiobacter*), *A. rhizogenes*, *A. rubi* and *A. vitis*, together with *Allorhizobium undicola*, form a monophyletic group with all *Rhizobium* species, based on comparative 6S rDNA analyses. *Agrobacterium* is an artificial genus comprising plant-pathogenic species. The monophyletic nature of *Agrobacterium*, *Allorhizobium*, and *Rhizobium*, and their common phenotypic generic circumscription support their amalgamation into a single genus, *Rhizobium*. The classification and characterization of *Agrobacterium* strains including differentiation of *A tumefaciens* and *A rhizogenes* and their various opine-type classes is a practice well known in the art (see, for example, Laboratory guide for identification of plant pathogenic bacteria, 3rd edition. (2001) N. W. Schaad, J. B. Jones, and W. Chun (eds.) ISBN 0890542635; for example, the article of Moore et al. published therein).

Recent analyses demonstrate that classification by its plant-pathogenic properties is not justified. Accordingly, more advanced methods based on genome analysis and comparison (such as 16S rRNA sequencing; RFLP, Rep-PCR, etc.) are employed to elucidate the relationship of the various strains. Agrobacteria can be differentiated into at least three biovars, corresponding to species divisions based on differential biochemical and physiological tests. Pathogenic strains of *Agrobacterium* share a common feature; they contain at least one large plasmid, the tumor- or root-inducing (Ti- and Ri-, respectively) plasmid. Virulence is determined by different regions of the plasmid including the transferred DNA (TDNA) and the virulence (vir) genes. The virulence genes mediate transfer of T-DNA into infected plant cells, where it integrates into the plant DNA. According to the "traditional" classification, Agrobacteria include, but are not limited to, strains of *Agrobacterium tumefaciens*, (which by its natural, "aimed" Ti plasmid typically causes crown gall in infected plants), *Agrobacterium rhizogenes* (which by its natural, "armed" Ri-plasmid causes hairy root disease n infected host plants), *Agrobacterium rubi* (which in its natural, "armed" form causes cane gall on Ruhus), *Agrobacterium vitis*, and *Agrobacterium radiobacter*. The *Agrobacterium tumefaciens* cells and strains of the present disclosure do not comprise a wild-type Ti plasmid and/or a wild-type Ri plasmid.

*Agrobacterium*-mediated transformation is a process of using *Agrobacterium tumefaciens* to transfer a gene of interest into host cells, generally plant but not limited to that kingdom. Hereafter, plants will be discussed as the host organism. In a transient transformation the transferred DNA remains transiently in the nucleus while still being transcribed into desirable gene products. In a stable transformation the transferred DNA is integrated into the plant genome for inheritance into the next generation, generating transgenic plants.

Until the present application, there was neither a report of a wild type or a disarmed 1416 *Agrobacterium* strain, nor the documented use of such a strain in plant transformation. The wild type and the disarmed 1416 *Agrobacterium* strain of the disclosure are advantageous for generating transgenic plants that satisfy global regulatory and commercial requirements. The wild type and the disarmed 1416 *Agrobacterium* strain of the disclosure are useful for the efficient transformation of citrus tissue.

*Agrobacterium* strain 1416 was found to produce numerous galls (78%) in infected tissues and was considered the most effective when compared to other *Agrobacterium* strains used for transformation. Interestingly this strain showed no *Agrobacterium* overgrowth or tissue necrosis in transformed tissues. In addition, mortality rate was exceptionally low in transformed tissues, proliferated and regenerated transgenic shoots similar to non-transformed regenerating tissue. Of interest was the fact that transgenic shoots regenerated directly from transformed tissues, and indirectly from galls with high frequency averaged 42%. Furthermore, 1416 *Agrobacterium* strain was efficient in transferring DsRed and produced galls in internodal segments of mature tissues from Mexican lime (70%), lemon (48%), navel orange (25%) and clementine (6%). Finally, sequence and PCR analyses revealed that that strain 1416 is a novel strain and based on key findings in this strain, coupled with optimized transformation procedure, this strain is highly efficient in citrus transformation.

Many techniques are used to study gene expression in cells. Fluorescent proteins are widely used as reporters for gene expression. These proteins emit a detectable fluorescent light of a characteristic color when illuminated with certain light wavelengths. Nucleotides encoding fluorescent proteins may be placed under the regulatory sequences of a gene of interest and can then be used to report on the expression of that gene. The green fluorescent protein (GFP) was discovered in the early 1960s and used for tracking gene expression in bacteria and the sensory neurons of the nematode *C. elegans*. Genes encoding other fluorescent proteins useful as gene expression reporters have since been isolated and/or genetically engineered. A gene encoding a fluorescent protein emitting in the red spectrum was obtained from a reef coral *Discosoma* sp., and its protein was named DsRed (M V Matz, et al., 1999, "Fluorescent Proteins from Non-bioluminescent Anthozoa Species," Nature Biotechnology 17: 969-973). The gene encoding this protein has been introduced into a binary vector to assist in the determination of positive transformation using Agrobacteria.

A map of binary vector pCTAGV-KCN3 is depicted in FIG. 1. Starting at the 12 o'clock position and in a clockwise orientation, the pCTAGV-KCN3 vector contains DNA sequences corresponding to the stability protein from the plasmid pVS1 (pVS1 StaA); the replication protein from plasmid pVS1 (pVS1 RepA); the basis of mobility site (bom); an origin of replication (ori)*; a kanamycin resistance gene (KanR)*; an *Agrobacterium* left border T-DNA repeat (LB T-DNA repeat); a dissociation element 2 (DS element 2); an attP(phiC31) site (C31 attP); an attP(Bxb1) site (Bxb1 attP); a termination signal (Term)*; a NOS terminator (Nos Term); the BAG4 anti apoptosis gene (BAG4m)*; a 2A self-cleaving peptide (2A); marker gene DsRed (DSred)* under the control of GmUbi3 promoter with intron (GmUbi3 promoter 880)*; double CaMV35S promoter (db35S); a fusion of selectable marker genes CodA and NptII (CodA::NPTII); a CaMV35S poly A terminator (35S Term); a loxP(Cre) site (loxP); a dissociation element 1 (DS element 1); and the *Agrobacterium* right border T-DNA repeat (RB T-DNA repeat). Sequences indicated with an asterisk are in a different orientation than the remaining sequences.

*Citrus* is a plant of the family Rutaceae, sub family Aurantoidae. There are at least five commercially important citrus crops: orange, citron, grapefruit, lemon, and lime. An orange may be a sweet orange or a bitter orange; and a sweet orange may be a common orange, a blood orange, a naval orange, or an acid-less orange. Mandarin is found among the sweet orange varieties, and Satuma, tangerine, and clementine are some of its cultivars. A bitter orange may be at least one of a Seville orange, a Bergamot orange, or a trifoliate orange. Citron is the oldest variety of citrus, and there are at least three different groups of citron. Acid citron, sweet citron, and pulpless citron. There are at least seven varieties of grapefruit: white, pink, melogold, cocktail, red pomelo, oro blanco, and valentine. Many different varieties of lemons are known, for example, Avalon lemons, Lisbon lemons, eureka lemons, Meyer lemons, Sorrento lemons, citron lemons, Mediterranean Sweet lemon, Verna lemons, and Fino lemons. Similarly, there are many different varieties of limes, including Mexican lime, Australian finger lime, Tahiti lime, Kaffir lime, Rangpur lime, Calamansi lime, and lemon-lime.

Figure 2A:
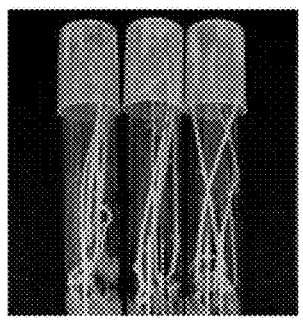
FIG. 2A to FIG. 2I depict images of CrZ epicotyl explants at the different stages during *Agrobacterium*-mediated transformation and regeneration of transgenic shoots.
Figure 2B:
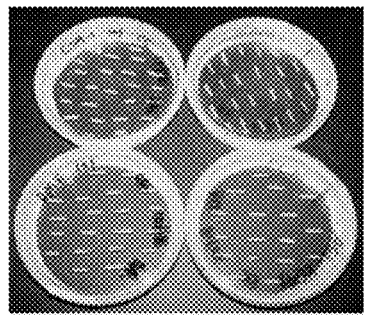
Figure 2C:
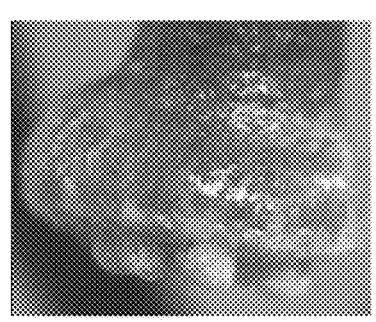
Figure 2D:
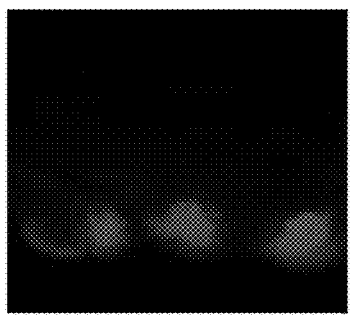
Figure 2E:
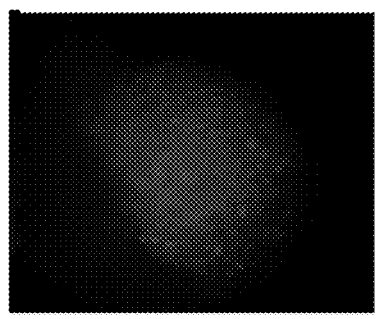
Figure 2F:
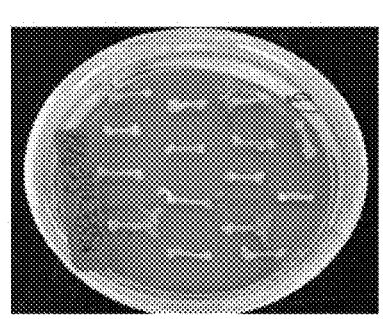
Figure 2G:
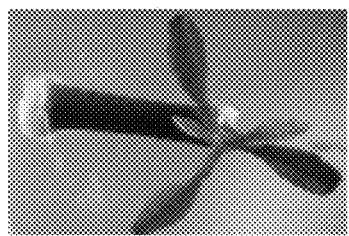
Figure 2H:
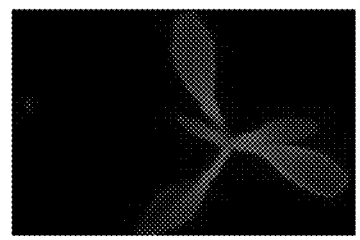
Figure 2I:
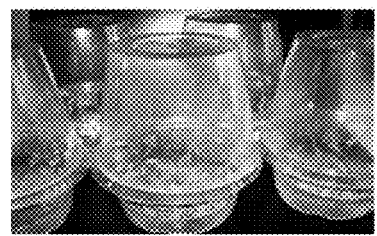

FIG. 2A to FIG. 2I depict the steps performed for the instant application during *Agrobacterium*-mediated transformation of CrZ epicotyl explants and the regeneration of transgenic shoots. FIG. 2A shows germinated CrZ seedlings; FIG. 2B shows transformed explants cultured on kanamycin selection media; FIG. 2C shows proliferated cells from transformed cut side of the epicotyl; FIG. 2D and FIG. 2E show DsRed expression in proliferated cells; FIG. 2F shows shoot regeneration on selection media; FIG. 2G shows a putative regenerated shoot; FIG. 2H shows uniform DsRed expression from a transgenic shoot; and FIG. 2I shows shoot elongation and rooting of transgenic CrZ shoots.

As seen in FIG. 3A to FIG. 3F, epicotyls of CrZ citrus explants transformed with *Agrobacterium* strains 1104; 159; 1526; 1416; 1565; and EHA105 carrying pCTAG-KCN3 expressing DsRed. And, as seen on FIG. 4 white bars, according to initial data from first set of transformation DsRed transient expression, strain 1416 showed the highest frequency (67%) followed by EHA105 (63%), 159 (23%), 1526 (6%), and 1104 (3%). After two rounds on selection regeneration media (SRM), it was observed that some of the tissues transformed with strains 1416 and 159 had proliferated around the vascular cambium cells layer, and produced callus/tumors around these tissues.

Figure 5A:
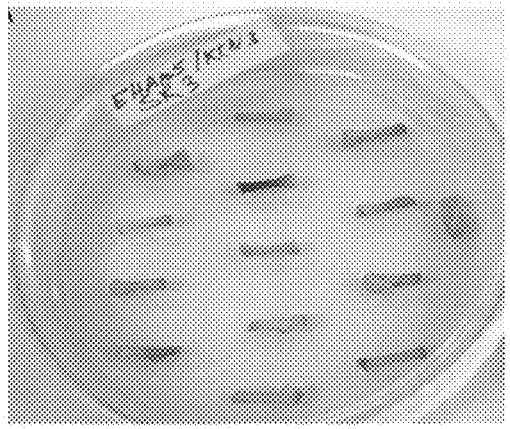
FIG. 5A to FIG. 5F depict images of the tissue responses after transformation with different *Agrobacterium* strains.
Figure 5B:
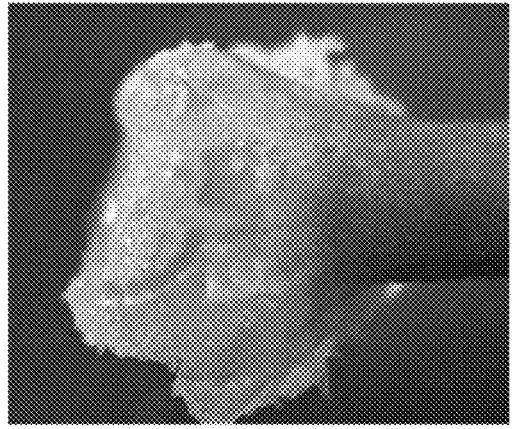
Figure 5C:
Figure 5D:
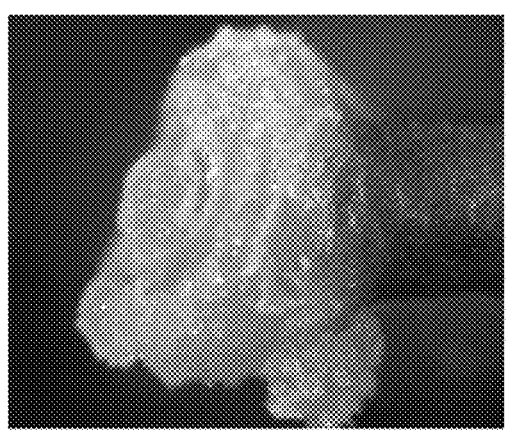
Figure 5E:
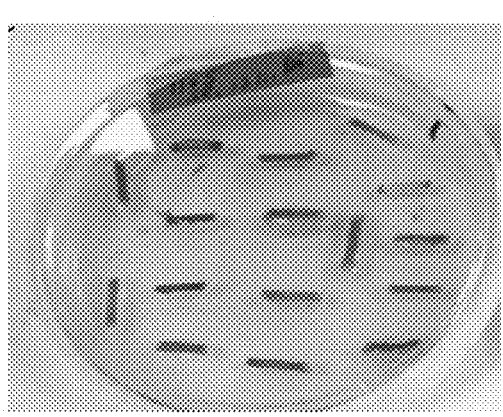
Figure 5F:
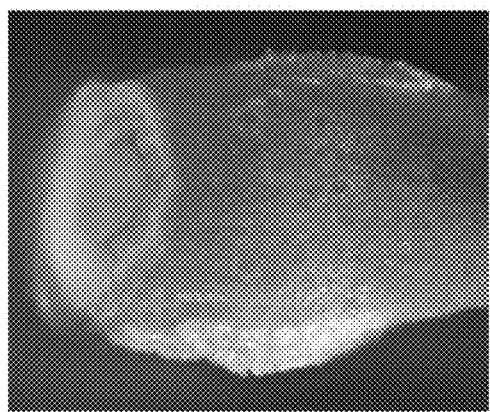
Figure 6:
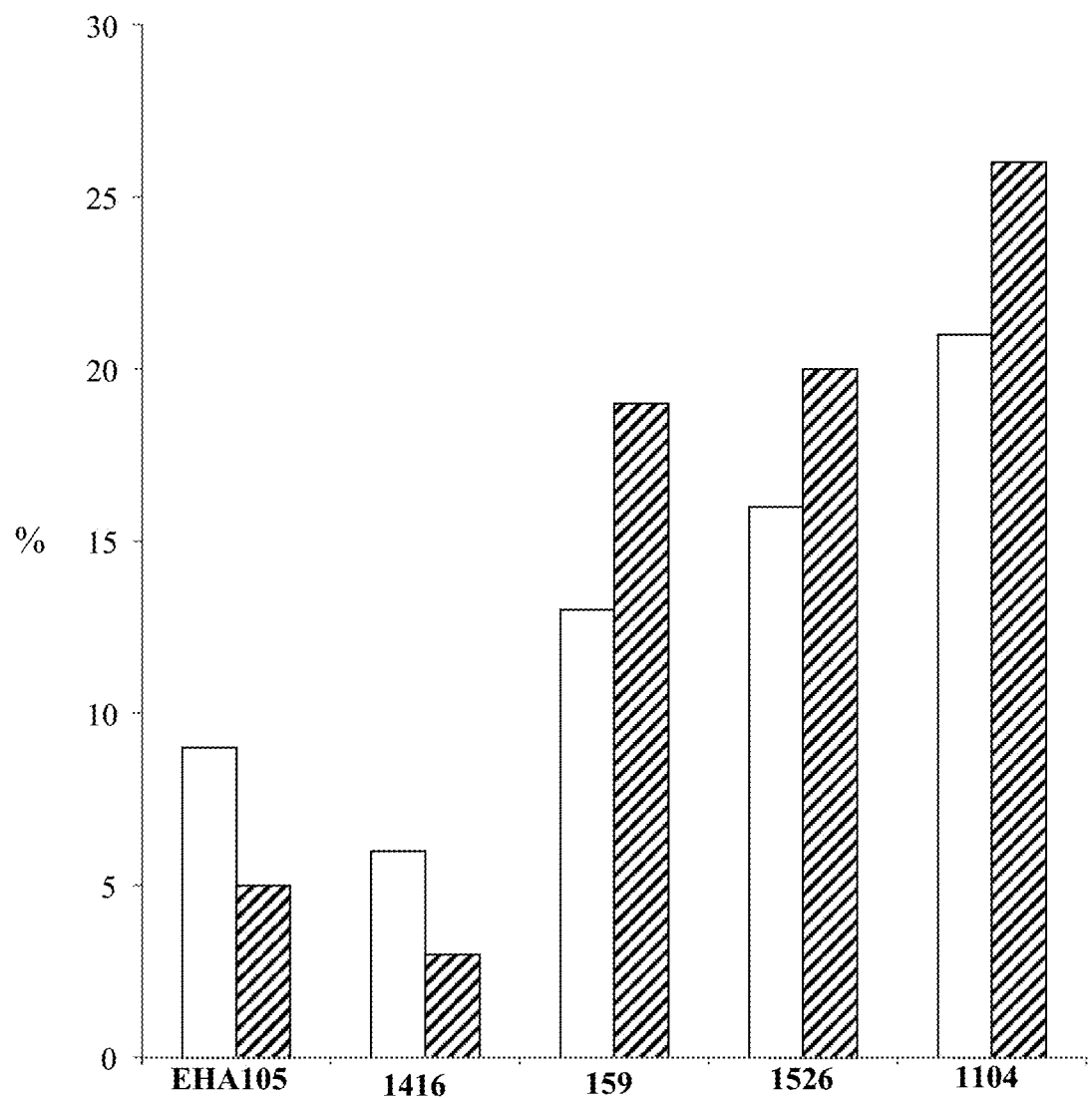
FIG. 6 depicts a graph of the average mortality rate of CrZ tissues after transformation with different *Agrobacterium* strains in the presence and absence of surfactant. The Y Axis presents the percentage (%) of dead plants. The X Axis presents the *Agrobacterium* strains used. White bars present results for tissues transformed in the absence of surfactant, bars with diagonal stripes present results for tissues transformed in the presence of surfactant.
Figure 7A:
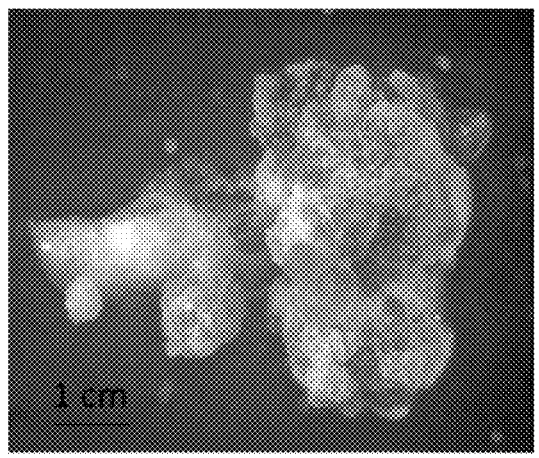
FIG. 7A to FIG. 7D depict images of tumors formed and stable DsRed expression in CrZ epicotyls transformed with wildtype *Agrobacterium* strains.
Figure 7B:
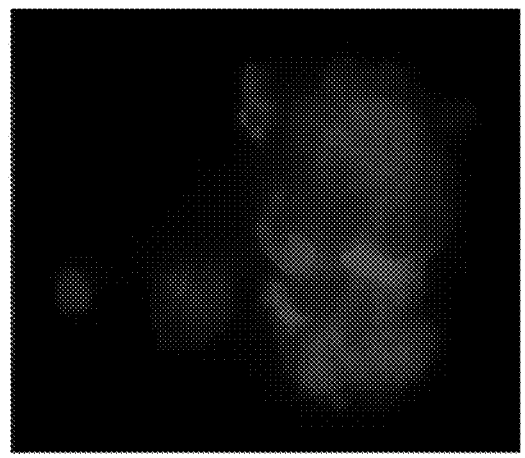
Figure 7C:
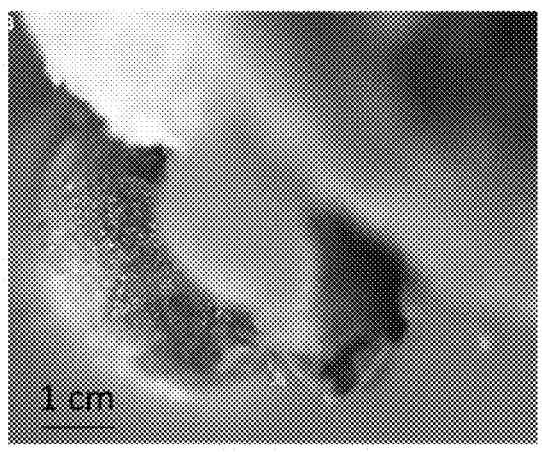
Figure 7D:
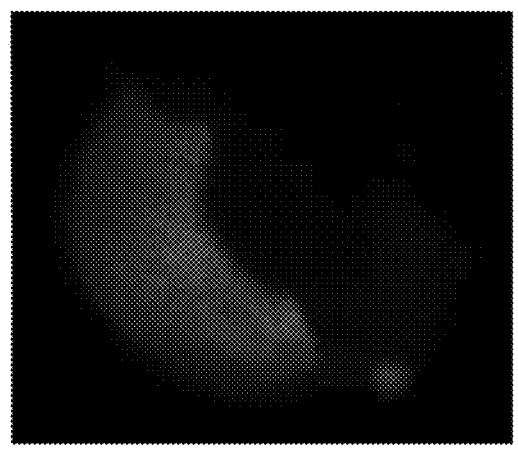
Figure 12:
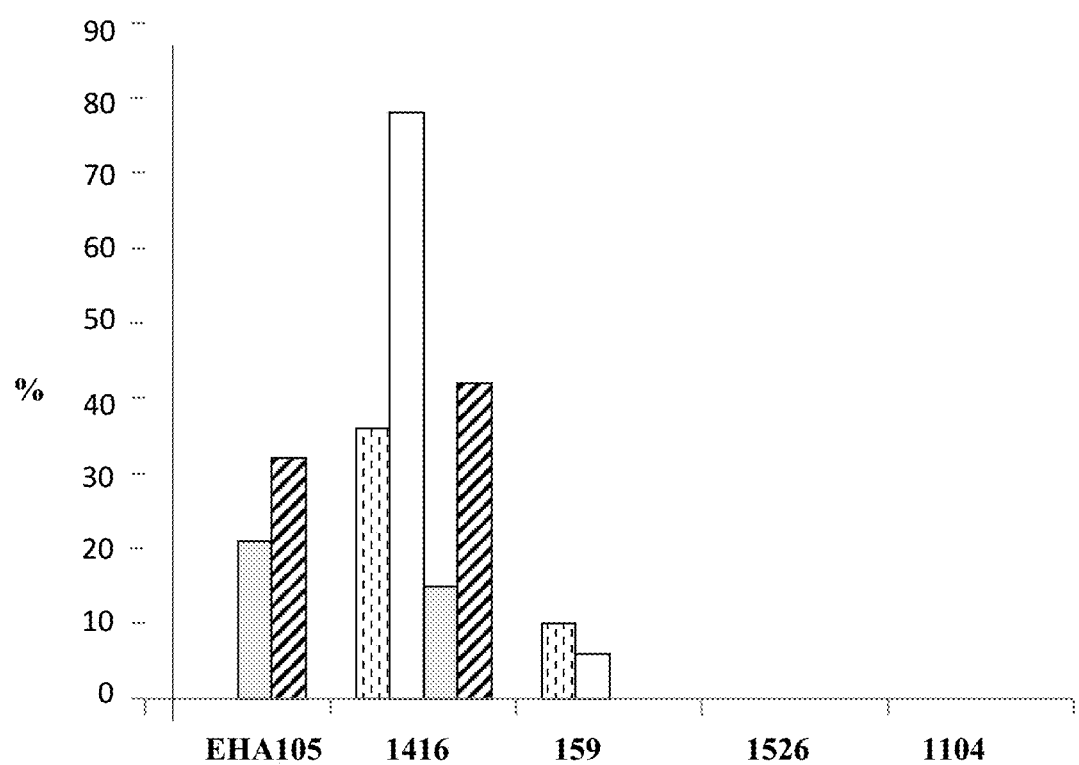
FIG. 12 depicts a graph of the effect of surfactant on the average gall formation and transformation frequency from CrZ epicotyls transformed with different *Agrobacterium* strains in the presence or absence of surfactant. Y axis shows the percentage galls or percentage of shoots regenerated. The X axis presents the different *Agrobacterium* strains used. Grey bars indicate transgenic shoots formed in the absence of surfactant; bars with diagonal stripes indicate transgenic shoots formed in the presence of surfactant; bars with vertical stripes indicate gall formation in the absence of surfactant; white bars indicate gall formation in the presence of surfactant.

See for example, FIG. 5C which shows health tissue transformed with 1416, and FIG. which shows proliferating tissues transformed with 1416. On the other hand, no tumors were observed formed from tissues transformed with EHA105, 1104, or 1526. See for example, FIG. which shows healthy tissue transformed with EHA105, FIG. 5B which shows proliferating tissue transformed with EHA105, FIG. 5E which shows healthy tissue transformed with 1104, and FIG. 5F which shows bacterial overgrowth, and necrotic and dying tissues transformed with wildtype 1104. In addition, with time, DsRed expression disappeared from tissues transformed with 1104 and 1526. The frequency of tumor formation was higher from 1416 (36%) than from 159 (10%). Although gall size was larger from 1416 than from 159, the difference was not measured. As seen in FIG. 7A to FIG. 7D, tumors formed in CrZ epicotyls transformed with wildtype *Agrobacterium* strains 1416 and 159 presented stable DsRed expression. FIG. 7A presents an image of tumors formed when transformed with wildtype strain 1416; FIG. 7B presents an image of the DsRed expression in tissues transformed with wildtype strain 1416; FIG. 7C presents an image of tumors formed when transformed with wild type strain 159; FIG. 7D presents an image of the DsRed expression in tissues transformed with wildtype strain 159. Six to eight weeks later, DsRed expressing shoots were observed regenerating from only tissues transformed with strains EHA105 and 1416. As seen in FIG. 12, the frequency of transgenic shoot regeneration was highest from EHA105 (21%) followed by 1416 (15%)

Figure 4:
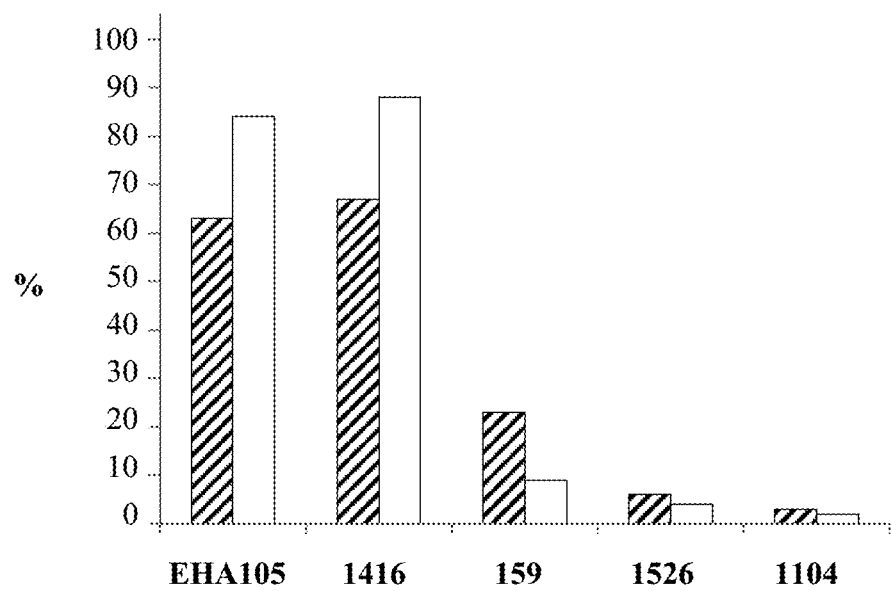
FIG. 4 depicts a graph of the frequency of DsRed expression in CrZ epicotyls transformed with different *Agrobacterium* strains, in the absence and presence of a surfactant. The Y Axis presents the percentage (%) of plants expressing DsRed. The X Axis presents the *Agrobacterium* strains used. Bars with diagonal stripes present results for tissues transformed in the absence of surfactant, white bars present results for tissues transformed in the presence of surfactant.

As shown in FIG. 4, DsRed expression frequency increased when Agrobacterium transformation with EHA105 and 1416 was performed in the presence of surfactant, while it decreased when Agrobacterium transformation with 159, 1526, or 1104 was performed in the presence of surfactant. DsRed expression frequency increased significantly in tissues transformed with 1416 (88%) and EHA105 (84%), while it decreased in tissues transformed with 159 (9%), 1526 (4%), or 1104 (2%).

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

As used herein, the term "about" is defined as plus or minus ten percent of a recited value. For example, about 1.0 g means 0.9 g to 1.1 g.

As used herein, the term "nucleic acid" refers to deoxyribonucleic acid (DNA) or ribonucleic acid (RNA).

The terms "selectable marker" and "screenable marker" are used interchangeably herein, and refer to a nucleic acid sequence whose expression confers a trait suitable for artificial selection facilitating the identification of cells, tissues, or plants containing the nucleic acid sequence.

As used herein, "transformation" refers to a process of introducing an exogenous nucleic acid into a cell or tissue. The transformation may be transient or stable. In stable transformations, part or all of the exogenous nucleic acid is incorporated (e.g., integrated or stably maintained) in the nuclear genomic DNA, plastid DNA, or is capable of autonomous replication in the nucleus or plastid.

As used herein, the term "symbiont" refers to a plant cell or a plurality of plant cells comprising at least one polynucleotide encoding at least one phytohormone biosynthetic enzyme and a polynucleotide of interest. The at least one phytohormone biosynthetic enzyme may be a cytokinin biosynthetic enzyme and/or an auxin biosynthetic enzyme. The cells of a symbiont autonomously divide due to the expression of the at least one polynucleotide encoding at least one phytohormone biosynthetic enzyme. A symbiont may comprise any number of cells, from 1 cell to 100,000 or more cells. The cells of a symbiont autonomously divide, forming an undifferentiated multi-cellular structure on a plant. The undifferentiated multicellular structure (symbiont) that is formed may be visually similar to a burl, a plant food body, a dormatia, an extrafloral nectary, a nodule, a plant neoplasm, or a gall, but are biochemically/genetically distinct by at least the transgenes expressed in the symbiont.

A symbiont may be removed from the original host plant, cultured in a laboratory setting, and/or transplanted onto another plant. When the symbiont, or at least one cell from the symbiont, is cultured, the "child symbiont material" may be used to refer to the new symbiont material formed over time and propagated from the original material removed from the host plant.

The terms "coding sequence," "coding region," and "open reading frame" are used interchangeably herein and refer to a region of continuous sequential nucleic acid triplets encoding a protein, a polypeptide, or a peptide sequence.

The terms "polyadenylation signal" and "polyA signal" are used interchangeably herein and refer to a nucleic acid sequence located 3' to a coding region that promotes the addition of adenylate nucleotides to the 3' end of an mRNA transcribed from the coding region.

The terms "promoter" and "promoter region" are used interchangeably herein and refer to a nucleic acid sequence, usually found 5' to a coding sequence, that alter expression of the coding sequence by providing a recognition site for RNA polymerase and/or other recognition sites for other transcription-related factors utilized to produce RNA and/or initiate transcription at the correct site on the DNA.

The terms "recombinant nucleic acid vector" and "vector" are used interchangeably herein and refer to any agent such as a plasmid, cosmid, virus, autonomously replicating sequence, phage, or linear or circular single- or double-stranded DNA or RNA nucleotide segment, derived from any source, capable of genomic integration or autonomous replication, comprising a nucleic acid molecule in which one or more nucleic acid sequences have been linked in a functionally operative manner. Such recombinant nucleic acid vectors or constructs typically comprise a 5' regulatory sequence or promoter region and a coding sequence encoding for a desired gene product. The vectors are typically designed such that once delivered into a cell or tissue, the coding sequence is transcribed into mRNA, which is optionally translated into a polypeptide or protein.

As used herein, the term "regeneration" refers to the process of growing a plant from a plant cell or tissue.

As used herein, the term "endogenous" refers to materials originating from within the organism or cell.

As used herein, the term "exogenous" refers to materials originating from outside of the organism or cell. As used herein, exogenous is intended to refer to any nucleic acid from a source other than the recipient cell or tissue, regardless of whether a similar (but not identical) nucleic acid may already be present in the recipient cell or tissue.

As used herein, the term "phenotype" refers to a trait exhibited by an organism resulting from the expression (or lack of expression) of nucleic acids in the genome (including non-genomic DNA and RNA such as plasmids and artificial chromosomes) and/or organelles of the organism.

As used herein, the term "transgenic" refers to organisms that have been stably transformed with an exogenous nucleic acid.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots". "Freshly emerging shoots" are shoots that have appeared as new growth on a plant in about the last 1 day, 2 days, 3 days, 4 days, 5 days, 6 days, 1 week, 2 weeks, 3 weeks, or 4 weeks.

Embodiments of the present disclosure are shown and described herein. It will be obvious to those skilled in the art that such embodiments are provided by way of example only. Numerous variations, changes, and substitutions will occur to those skilled in the art without departing from the disclosure. Various alternatives to the embodiments of the disclosure described herein may be employed in practicing the disclosure. It is intended that the included claims define the scope of the disclosure and that methods and structures within the scope of these claims and their equivalents are covered thereby. All publications, patents, and patent applications mentioned in this specification are herein incorporated by reference to the same extent as if each individual publication, patent, or patent application was specifically and individually indicated to be incorporated by reference.

EXAMPLES

Having now generally described this disclosure, the same will be better understood by reference to certain specific examples, which are included herein only to further illustrate the disclosure and are not intended to limit the scope of the disclosure as defined by the claims.

Example 1

Materials and Methods

Growing Wild Type *Agrobacterium* Strains

*Agrobacterium* strains were obtained from the retired collection of Dr. C. I. Kado (University of California, Davis, California, USA). All *Agrobacterium* strains used in this study were wild type except strain EHA105, a derivative of Strain C58/A281 which has the chromosomal background of C58 and the Ti-plasmid of pTi-bo542 (EE Hood, et al., 1993, "New *Agrobacterium* helper plasmids for gene transfer to plants," Transgenic Res. 2: 208-218; and D Sciaky, et al., 1978, "Fingerprints of *Agrobacterium* Ti plasmids," Plasmid 1: 238-253). As seen in Table 2, below, the wildtype *Agrobacterium* strains were obtained from several sources. Dry pellets of *Agrobacterium* gall cells were resuspended with 1 mL of liquid Luria Burtani (LB) media (J. Sambrook, et al., 1989, "Molecular cloning: a laboratory manual," 2nd ed. Cold Spring Harbor Laboratory Press, Cold Spring Harbor, N.Y), and then poured into additional 4 mL of LB media. Cultures were incubated using a shaker at 215 rpm at 28° C. for 2-3 days. Grown *Agrobacterium* cultures were then streaked onto LB media plates to obtain single colonies. Plates were incubated at 28° C. for 2-3 days. Liquid YEP media in 50 mL tubes were inoculated with single *Agrobacterium* colonies and were incubated in shaker at 215 rpm at 28° C. for 2-3 days to assure purity of *Agrobacterium* cells.
Determining Antibiotic Selection for *Agrobacterium* Strains

*Agrobacterium* strains cultures (150 μL) were spread onto LB media plates without antibiotics, or containing 100 mg/L kanamycin, 150 mg/L spectinomycin, 200 mg/L gentamycin, 100 mg/L ampicillin, or 250 mg/L carbenicillin. All plates were incubated at 28° C. for 3 to 4 days. Bacterial growth was then observed and recorded as susceptible or resistant to the antibiotic used.
Preparing *Agrobacterium* Competent Cells Single colonies from LB media plates of *Agrobacterium* strains were used for the inoculation of 10 mL of liquid LB media in 50 mL tubes were incubated for at 28° C. for 2-3 days. The Optical Density reading (OD) of bacterial cells was measured and adjusted to nm 0.8 to 1.0 at 600 nm using a BIO-RAD SMARTSPEC 3000 spectrophotometer (Bio-Rad; Hercules, California, USA). Cultures were centrifuged at 4500 rpm for 10 minutes at 4 to 6° C. Pellets were then resuspended well with 10 mL of 10% cold glycerol and kept on ice. The centrifugation and resuspension of pellets were repeated two times with 5 mL and 2.5 mL 10% cold glycerol. Finally, 50 μL bacteria cultures were aliquoted into 1.5 mL EPPENDORF tubes, immersed in liquid nitrogen and kept in a −80° C. freezer.

*Agrobacterium* Strains and Control Vector

Binary vector pCTAGV-KCN3 of a pCAMBIA background, contains a DsRed marker gene and a neomycin phosphotransferase selectable marker gene (NptII). FIG. 1 depicts a schematic diagram for control vector pCTAGV-KCN3. In a clock-wise orientation, the pCTAGV-KCN3 vector depicted in FIG. 1 contains DNA sequences corresponding to the PVS1 StaA; pVS1 RepA; bom site; origin of replication*; kanamycin resistance gene*; *Agrobacterium* left border (LB) T-DNA repeat (element 2); an attP(phiC31) site (C31 attP); an attP(Bxb1) site (Bxb1 attP); a termination signal (Term)*; a NOS terminator (Nos Term); the BAG4 anti apoptosis gene (BAG4m)*; a 2A self-cleaving peptide (2A); marker gene DsRed (DSred)* under the control of GmUbi3 promoter with intron (GmUbi3 promoter 880)*; double CaMV35S promoter (db35S); a fusion of selectable marker genes codA and nptII (CodA::NPTII); a CaMV35S poly A terminator (35S Term); a loxP(Cre) site (loxP); a dissociation element 1 (DS element 1); and the *Agrobacterium* right border (RB) T-DNA (DS element 1). Sequences indicated with an asterisk are in a different orientation than the remaining sequences.

One microliter of purified binary vector pCTAGV-KCN3 plasmid DNA was added to competent cells on ice, resuspended a few times, and then transferred to pre-chilled 1 mm electroporation cuvettes (BulldogBio; Portsmouth, New Hampshire, USA). Cells were electroporated at 1.7 kV Voltage, 25 μF Capacitance and 200 co Resistance using a BIO-RAD Gene Pulser (Bio-Rad, USA). After electroporation, cultures were transferred to 1.5 mL Eppendorf tubes containing 200 μL of YEP medium, and placed on a shaker at 215 rpm for 1 hour at 28° C. After incubation, liquid cultures were spread onto LB media plates containing 100 mg/L Kanamycin. Plates were incubated at 28° C. for 2-3 days. A grown colony from each strain/pCTAGV-KCN3 was used to inoculate 5 mL YEP liquid media containing 100 mg/L Kanamycin in 50 mL tubes. Tubes were then placed on shaker at 28° C. for 2-3 days. Finally, 50% glycerol stocks of constructs were made and placed in a −80° C. freezer.
Plant Material Carrizo'citrange (CrZ) (*Citrus sinensis×Poncirus trifoliata*) seeds and mature branches (12-14 inches) from greenhouse-grown adult plants of Mexican lime (*Citrus aurantifolia*), Washington navel orange (*Citrus sinensis* (L.)), Clementine (*Citrus reticulata*), and Lemon (*Citrus eureka*) were surface-sterilized with 20% bleach, shaken for 20 minutes, and rinsed 3 times with sterile water. CrZ seeds were then cultured into glass tubes containing MS media supplemented with vitamins, 3% sucrose, and solidified with 7.0 g/L agar (Sigma-Aldrich; St. Louis, Missouri, USA) for germination. The tubes were incubated at 26±1° C. in dark conditions for 3 weeks, and in a 16 hour-light/8 hour-dark cycle under soft white fluorescence light intensity of 50 μmol s$^{-1}$ m$^{-2}$ at 26° C. for 1 week prior to transformation. Lite greenish color epicotyls from CrZ seedlings were cut into 3-5 mm segments. Second flushes stem from mature citrus plants were sterilized as mentioned above, and internodal stem segments were cut into mm and used for transformation.
*Agrobacterium* Cultures and Plant Transformation A loop from frozen glycerol stocks of each *Agrobacterium* strain was inoculated into mL liquid YEP, and allowed to shake horizontally at 215 rpm at 28° C. for 2-3 days. Grown cultures were centrifuged for 9 minutes at 4000×G (Eppendorph 5414) at 18° C. Pellets were then resuspended in infection liquid media (INM) consisting of MS salts, 1 mL/l 1000× B5 vitamin, 2 mg/L glycine, 3% sucrose, 2 mg/L 2, 4-D, 2 mg/L BA, 200 µM acetosyringone, and a pH of 5.2. The OD of *Agrobacterium* cultures was adjusted to 0.2-0.4. Cultures were then placed on a shaker at 130 rpm at room temperature for 1 to 2 hours. In one set of experiments, *Agrobacterium* cultures were directly used for transformation. In another set of experiments, and before *Agrobacterium* inoculation, 0.01% was added to INM and grown for 16 hours. The OD of *Agrobacterium* cultures was adjusted to 0.2-0.4 and transformed. The tubes were inverted a few times and citrus CrZ epicotyls were inoculated with 10 mL cultures from the different *Agrobacterium* strains. Intermodal stem segments from mature Mexican lime, navel orange, clementine, and lemon were inoculated with 10 mL *Agrobacterium* 1416. All inoculations were performed for 10-15 minutes followed by 5 minutes shaking horizontally at room temperature. Transformed tissues were blotted on sterilized WHATMAN filter paper to remove excess bacteria. Tissues were then transferred to co-cultivation media consisting of MS salts, 1 mL/L 1000× B5 vitamin, 3% sucrose, 0.5 mg/L 2, 4-D (which was replaced by 0.5 mg/L NAA for Mexican lime and Clementine), 2 mg/L BA, 1 mg/L Kinetin, 150 µM acetosyringone, and 1.5 g/L GELRITE (Sigma-Aldrich). The pH was adjusted to 5.4 prior to autoclave. Cultures were incubated at 24° C. in the dark for 2-4 days.

Selection and Shoot Regeneration

After the co-cultivation period, explants were transferred to selection regeneration media (SRM1) consisting of DKW (Basal medium prepared according to J A Driver and A H Kuniyuki, 1984, "In Vitro Propagation of Paradox Walnut Rootstock," Hort. Science 19:507-509; 1 mL/L 1000× B5 vitamin, 3% sucrose, 6.0 g/L agar (Sigma-Aldrich), 300 mg/L vancomycin, 350 mg/L cefotaxime, 2 mg/L BA, 1 mg/L kinetin, 0.5 mg/L NAA, and 70 mg/L kanamycin with a pH of 5.7. The plates were incubated in the dark for 14-21 days at 26° C. Transient DsRed expression was examined and scored 10-12 days of after transformation. For shoot regeneration, the cultures were transferred to fresh selection regeneration media 2 (SRM2), same as SRM1 but without the addition of NAA and kinetin. (1 mL/L 1000× B5 vitamin, 3% sucrose, 6.0 g/L agar (Sigma-Aldrich), 300 mg/L vancomycin, 350 mg/L cefotaxime, 2 mg/L BA, and 70 mg/L kanamycin with a pH of 5.7). Cultures were incubated in 16 hour-light/8 hour-dark cycle under soft white fluorescence light intensity of 50 µmol s$^{-1}$ m$^{-2}$ at 26° C. for 14-21 days. Tissues were transferred to fresh SRM2 every 14 days. Stable DsRed expression was confirmed in tissues, galls, and regenerated shoots. After 6-8 weeks on SRM2, transgenic shoots that expressed stable, DsRed fluorescence were transferred onto shoot maintenance media (SMM2) for 3-4 weeks in 16 hour-light/8 hour-dark cycle under soft white fluorescence light intensity of 70 µmol s$^{-1}$ m$^{-2}$ at 26° C. The shoots were maintained until tissues were harvested for molecular analysis.

Confirming DsRed Expression

Expression of Red fluorescent marker gene DsRed was confirmed in transformed tissues and in regenerated shoots using Leica MZ 16F microscope at 1× magnification, and the appropriate filter for detection of the red fluorescence of the DsRed gene (filter 10447412). DsRed has an excitation maximum at 545 nm and emission maximum at 600 nm. Light source from Fluorescence Illumination System Xcite 120 (EXFO). The images were taken using a Q Leica camera with Q Capture software.

PCR Analysis of Galls and Regenerated Shoots Transformed with 1416

DNA was isolated from 50-100 mg segments of galls and regenerated shoots of transformed and non-transformed CrZ citrus according to PUREGENE plant tissues DNA isolation protocol. PCR analysis was performed for the presence of the nptII and kanamycin resistance (aph3) genes from binary vector pCTAGV-KCN3. Another set of PCR analysis was performed for pTi-1416 T-DNA genes and backbone sequences insertion beyond the right and left border of pTi-1416. PCR reactions were performed using 100 ng of template DNA and 10 ng of DNA from 1416/pCTAG-KCN3 (positive control), 2 µl of 5× Buffer, 2.5 mM Mgcl2, 0.25 mM dNTP's, 1 unit Go Taq polymerase (Promega; Madison, Wisconsin, USA) and 2 pM of forward and reverse primers listed in Table 1, in 20 µL reactions. PCR cycle conditions were set as the following: Initial denaturation at 94° C. for 3 minutes, followed by 30 cycles consisting of 94° C. denaturation for 45 seconds, annealing at 58° C. for 45 seconds, extension at 72° C. for 2 minutes, and a final extension at 72° C. for 5 minutes. Finally, the PCR products were loaded into ethidium bromide stained 0.8% gel for electrophoresis and observed on a UV light box.

Sequencing of *Agrobacterium* Strains

Genomic DNA was isolated from four *Agrobacterium* strains which scored positive for citrus transformation, using Qiagen Blood & Cell Culture DNA Maxi Kit #13362 and Genomic DNA Buffer Set #19060. (Qiagen, Germany). DNA samples were then evaluated by gel electrophoresis, and quantified by using, both, a 2100 NANODROP spectrophotometer (Thermo Fisher Scientific; Waltham, Massachusetts, USA) and a QUBIT fluorimeter (Invitrogen; Waltham, Massachusetts, USA) using the QUBIT dsDNA HS Assay Kit (Invitrogen). The genomic DNA was sheared with g-TUBE (Covaris; Woburn, Massachusetts, USA). A 20-kb DNA library was constructed according to the manufacturer's instructions and sequenced using single-molecule real-time (SMRT) sequencing technology on the PACBIO RS System (PacBio; Menlo Park, California, USA). De novo genome assembly was conducted with the latter using the Hierarchical Genome Assembly Process (HGAP) workflow (SMRT Portal; Pacific Biosciences; Menlo Park, California, USA), protocol "RS_HGAP_Assembly.3" Sequences were entered into the National Center for Biotechnology Information (NCBI) and Rapid Annotation using Subsystem Technology (RAST), and were used for sequence analysis and gene annotation.

Confirming Ti-Plasmid Type by PCR Analysis

PCR amplifications of Ti-plasmid identity genes were performed for eight (8) wild type *A. tumefaciens* strains and 2 disarmed strains (EHA105 and LBA4404) used as controls. Genomic DNA from *Agrobacterium* strains cultures was isolated according to the GENTRA PUREGENE protocol (Qiagen; Germantown, Maryland, USA). Twenty ng/ill of DNA was used with GoTaq DNA Polymerase (Promega; Madison, Wisconsin, USA), and PCR reactions were performed as described above. All primer sets used for the amplifications are listed in Table 1. PCR amplification cycles were: 94° C. for 3 minutes, 30 cycles of 94° C. for 45 seconds, 58° C. for 45 seconds, and 72° C. for 2 minutes, followed by final extension at 72° C. for 5 minutes. The amplified DNA was analyzed by ethidium bromide stained 0.8% agarose gel electrophoresis and observed on a UV light box.

Disarming *Agrobacterium* Strain 1416—Creation of 1416G

Figure 17:
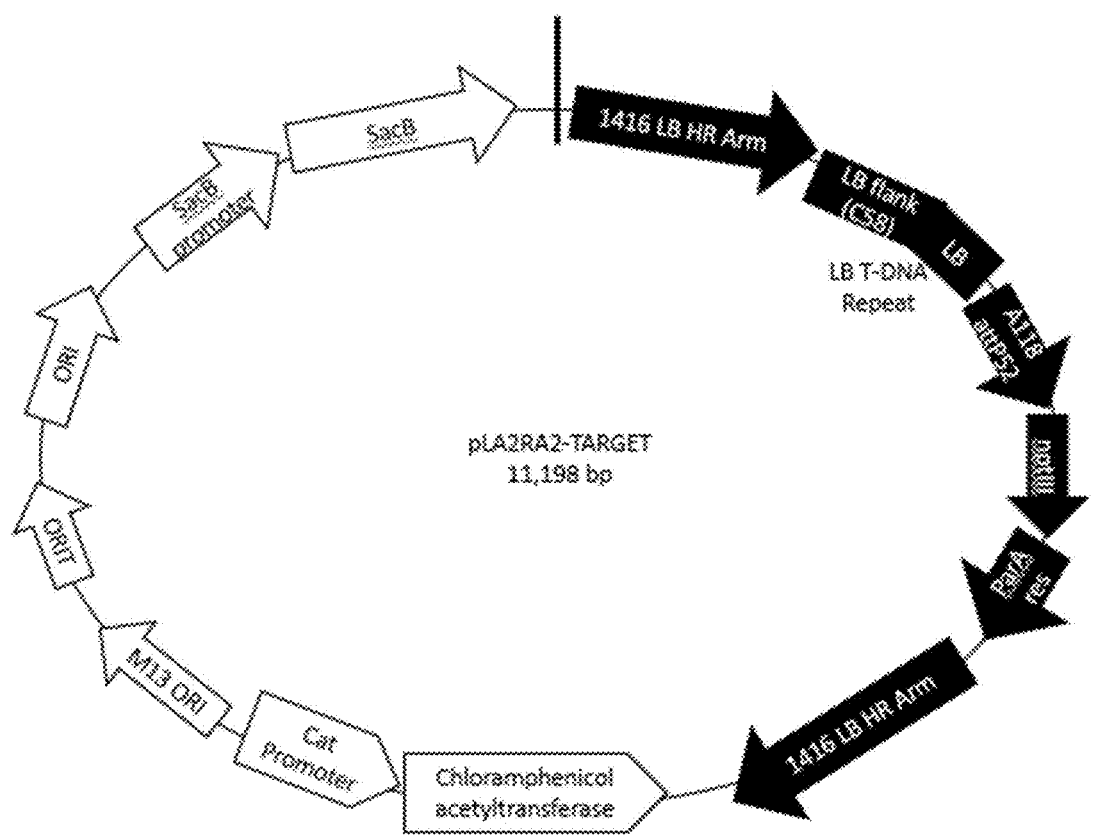
FIG. 17 depicts a map of pLA2RA2-TARGET. Starting at the 12 o'clock position and in a clock-wise orientation, pLA2RA2-TARGET contains the 1416 LB HR arm; C58; LB; A118 attP52; nptIII (kanamycin resistance); ParA res; 1416 LB HR Arm; chloramphenicol acetyltransferase under the control of the Cat promoter*; M13 Ori; ORIT; ORI; SacB promoter; and SacB. *The Cap promoter and chloramphenicol acetyltransferase read in the opposite orientation from the rest of the polynucleotides.

Border sequence deletions of *Agrobacterium* strain 1416 were performed using border-removal plasmid pLA2RA2-TARGET. A map of pLA2RA2-TARGET is depicted in FIG. 17, and comprises a 1075 bp of genome homology sequence of the 1416 LB HR Arm used for precise homologous recombination targeting of the T-DNA gall forming domain of the 1416 virulence plasmid and replacement with the GAANTRY technology; the 238 bp LB flank (C58) and 25 bp LB T-DNA repeat region obtained from the native C58 genome and required for T-DNA transfer. The 25 bp LB T-DNA repeat region is required and the 238 bp LB flank (C58) may enhance the fidelity of T-DNA transfer; a 52 bp attP(A118) site (A118 attP); a 795 bp aminoglycoside phosphotransferase gene (nptIII) that provides kanamycin resistance to microbes; 106 bp res(ParA) site (ParA resolution site); the 1416 RB HR Arm containing 1110 bp of 1416 homology sequence used for precise genome targeting, gall gene removal and replacement with GAANTRY technology. Vector pLA2RA2-TARGET contains the SacB gene as a negative selectable marker for *A. tumefaciens*, and a kanamycin resistance (aph3) gene as a positive selectable marker for *A. tumefaciens*. Approximately 100 ng/μl of pLA2RA2-TARGET was electroporated into *A. tumefaciens* 1416 competent cells. Culture was spread onto LB media plates containing 50 mg/l kanamycin. Positive colonies were confirmed by PCR and sequencing. Two colonies were chosen for liquid culture and later streaked onto LB media plate containing 5% sucrose and 50 mg/l kanamycin.

Figure 18:
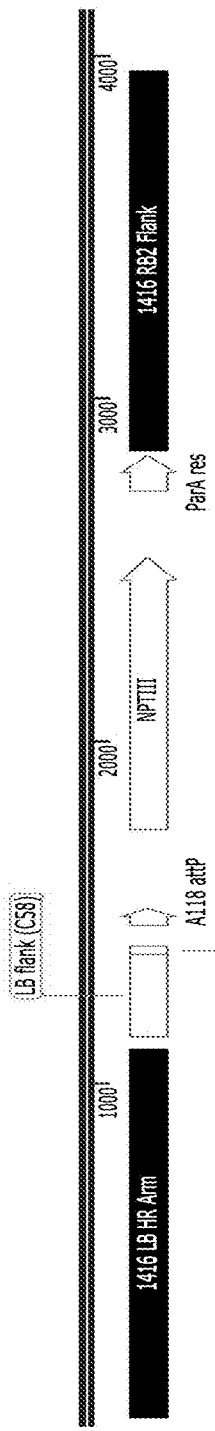
FIG. 18 depicts a map of a portion of 1416G, a disarmed strain derived from *Agrobacterium* strain 1416 wild type. The figure shows portions corresponding to the 1416 LB HR Arm; the 238 bp LB flank (C58) and the 25 bp LB T-DNA repeat region obtained from the native C58 genome; a 54 bp attP(A118) site (A118 attP); a 795 bp neomycin phosphotransferase gene that provides kanamycin resistance to microbes; a 106 bp res(ParA) site (ParA resolution site); and the 1416 RB HR Arm.

FIG. 18 depicts a map of a portion of 1416G, a disarmed strain derived from *Agrobacterium* strain 1416. Strain 1416G comprises the 1416 LB HR Arm containing 1075 bp of genome homology sequence used for precise genome targeting of the GANNTRY technology; the 238 bp LB flank (C58) and 25 bp LB T-DNA repeat region obtained from the naïve C58 genome and required for T-DNA transfer. A 52 bp attP(A118) site (A118 attP); a 795 bp aminoglycoside phosphotransferase gene (nptIII) that provides kanamycin resistance to microbes; 106 bp res(ParA) site (ParA resolution site); the 1416 RB HR Arm containing 1110 bp of 1416 homology sequence used for precise genome targeting, gall gene removal and replacement with GAANTRY technology. This strain was designed to be used with the GAANTRY T-DNA stacking technology and transformation.

Figure 19:
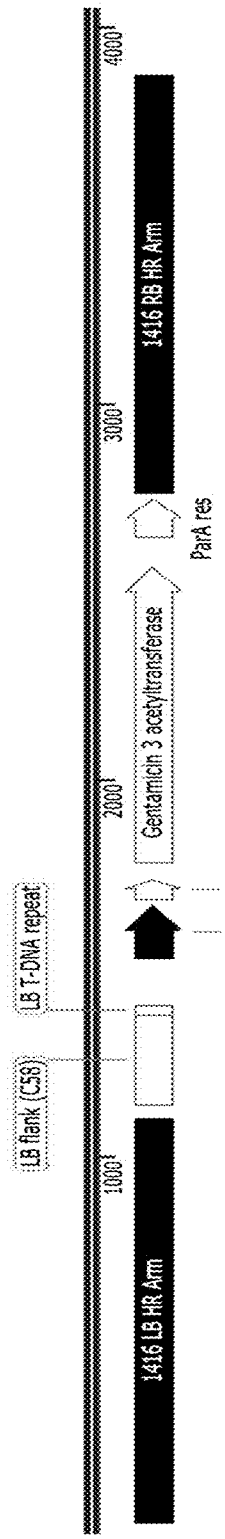
FIG. 19 depicts a map of a portion of 1416G-NRB3, a disarmed strain derived from *Agrobacterium* strain 1416G generated via the GAANTRY site-specific recombination system. The figure shows portions corresponding to the 1416 LB HR Arm; the 238 bp LB flank (C58) and the 25 bp LB T-DNA repeat region obtained from the native C58 genome; the 145 bp tomato pectinase TermA2; a 55 bp attB(TP901) site (TP901 attB); a 789 bp Gentamicin 3 acetyltransferase gene that provides gentamicin resistance to microbes; a 106 bp res(ParA) site (ParA resolution site); and the 1416 RB HR Arm.

FIG. 19 depicts a map of a portion of 1416G-NRB3, a disarmed strain derived after 1416G via GAANTRY. The original kanamycin selection gene (nptIII gene) was swapped out and the gentamycin gene (aacC1) swapped in. Strain 1416G-NRB3 comprises the 1416 LB HR Arm containing 1075 bp of genome homology sequence used for precise genome targeting of the GANNTRY technology; the 238 bp LB flank (C58) and 25 bp LB T-DNA repeat region obtained from the naïve C58 genome and required for T-DNA transfer. More specifically, the 25 bp LB T-DNA repeat region is required, and the 238 bp LB flank (C58) may enhance the fidelity of T-DNA transfer; the 145 bp Tomato pectinase TermA2 is a tomato terminator added to provide transcriptional insulation from the surrounding genome on the T-DNA/GAANTRY assembly domain); a 55 bp attB (TP901) site (TP901 attB); a 789 bp Gentamicin 3 acetyltransferase gene that provides gentamicin resistance to microbes; the 106 bp res(ParA) site (ParA resolution site); and the 1416 RB HR Arm containing 1110 bp of genome homology sequence used for precise genome targeting of the GAANTRY technology. This strain was designed to be used with either binary vector (kanamycin or spectinomycin based selection) transformation or GAANTRY T-DNA stacking technology and transformation.

Example 2

*Citrus* Tumor Formation and Shoot Regeneration

Twenty-five wild type *Agrobacterium* strains were tested for their ability to transform CrZ epicotyl seedling segments.

Forty-five wild type *Agrobacterium* strains collected from different plant species and soils were initially attempted for re-growth from dry pellets. Out of the forty-five strains, twenty-five strains grew in LB liquid media without antibiotics.

Binary vector pCTAGV-KCN3 has the intron-containing DsRed gene, and the kanamycin resistant gene inside both border sequences. A representation of this vector is shown in FIG. 1. This binary vector was introduced into *Agrobacterium* strains by electroporation, and CrZ epicotyl segments from seedlings were transformed with the twenty-five strains. FIG. 2A to FIG. 2I depict images of the different steps of the *Agrobacterium*-mediated transformation of CrZ epicotyl explants and regeneration of transgenic shoots. FIG. 2A shows germinated CrZ seedlings; FIG. 2B shows transformed explants cultured on kanamycin selection media; FIG. 2C shows proliferated cells from transformed cut side of the epicotyl; FIG. 2D and FIG. 2E show DsRed expression in proliferated cells; FIG. 2F shows shoot regeneration on selection media; FIG. 2G shows a putative regenerated shoot; FIG. 2H shows uniform DsRed expression on a transgenic shoot; FIG. 2I shows shoot elongation and rooting of transgenic CrZ shoots.

Transient DsRed expression in epicotyls of CrZ citrus explants showed differential responses to transformation, depending on the strain used. As indicated in Table 2 below, out of the 25 strains tested, eight strains showed DsRed transfer, and expressed at least one foci on transformed tissues. A plus sign (+) indicates that at least one DsRed positive foci was observed, a minus sign (−) indicates that no DsRed spots were observed in the transformed Carrizo epicotyls.

TABLE 2

STRAINS TESTED FOR CITRUS TRANSFORMATION

| Agrobacterium Strain I.D. # | Year Isolated | Source | Citrus transformation |
| --- | --- | --- | --- |
| 1D1299 | 1977 | Cherry | (−) |
| 1D1405 | 1968 | Poplar | (+) |
| 1D1409 | 1969 | Eucalyptus | (−) |
| 1D1411 | 1969 | Juniper | (+) |
| 1D1414 | 1979 | Loganberry | (−) |
| 1D1104 | 1972 | Poplar | (+) |
| 1D1562 | 1983 | Pear | (−) |
| 1D106 | Unknown | Unknown | (−) |
| 1D159 | 1970 | Peach soil | (+) |
| 1D198 | 1971 | Brown peach | (−) |
| 1D1144 | 1974 | Plum | (−) |
| 1D1526 | 1982 | Apple gall | (+) |
| 1D1563 | 1983 | Pear | (−) |
| 1D1564 | 1983 | Almond | (−) |
| 12D112 | 1976 | Norway Maple | (−) |
| 1D1491 | 1981 | Apple | (−) |
| 12D110 | 1976 | Peach | (+) |
| 1D1425 | 1980 | Grapevine | (−) |
| 1D1527 | 1982 | Apple gall | (−) |
| 1D1489 | 1981 | Apple | (−) |
| 1D1119 | 1975 | Grape (Octopine) | (−) |
| 1D1105 | 1972 | Sequoia | (−) |
| 1D1416 | 1972 | Euonymus Japonicum | (+) |
| 1D1565 | 1983 | Almond | (+) |
| 12D13 | 1974 | Redwood gall | (−) |

Figure 3A:
FIG. 3A to FIG. 3F depict images of DsRed expressed in epicotyls of CrZ citrus explants transformed with different *Agrobacterium* strains carrying pCTAGV-KCN3.
Figure 3B:
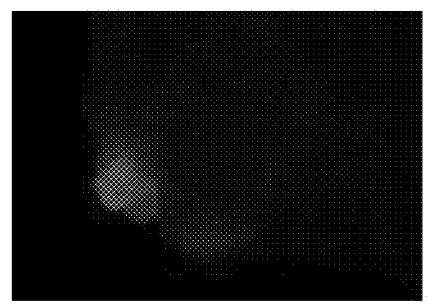
Figure 3C:
Figure 3D:
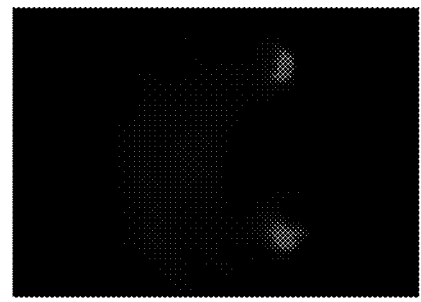
Figure 3E:
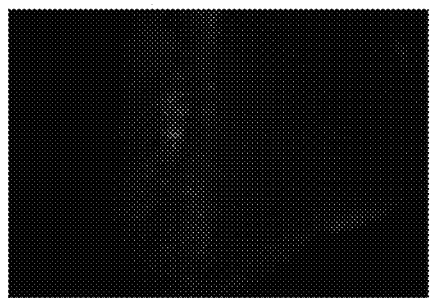
Figure 3F:
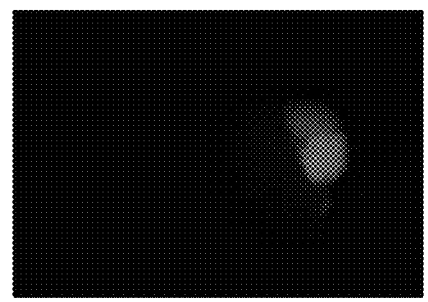

Fluorescent micrographs of CrZ citrus explants transformed with several of the *Agrobacterium* strains carrying pCTAGV-KCN3 and showing at least some DsRed transfer are depicted in FIG. 3A to FIG. 3F. An explant transformed with *Agrobacterium* 1104 is shown in FIG. 3A; an explant transformed *Agrobacterium* with 159 is shown in FIG. 3B; an explant transformed with *Agrobacterium* 1526 is shown in FIG. 3C; an explant transformed with *Agrobacterium* 1416 is shown in FIG. 3D; an explant transformed with *Agrobacterium* 1565 is shown in FIG. 3E; and an explant transformed with *Agrobacterium* EHA105, which was used as a positive control, is shown in FIG. 3F. These eight strains to which CrZ epicotyl tissues were responsive to were tested for their resistance to common antibiotics used in binary selection, and the results are shown Table 3 below.

TABLE 3

TESTED STRAINS ANTIBIOTIC RESISTANCE

| Agrobacterium Strain I.D. # | Kanamycin (100 mg/L) | Spectinomycin (150 mg/L) | Gentamycin (200 mg/L) | Ampicillin (100 mg/L) | Carbenicillin (250 mg/L) |
|---|---|---|---|---|---|
| 1D1405 | (−) | (−)/(+) | (−) | (+) | (−) |
| 1D1411 | (−) | (−) | (−) | (+) | (−) |
| 1D1104 | (−) | (+) | (−) | (+) | (−) |
| 1D159 | (−) | (−)/(+) | (−) | (+) | (−) |
| 1D1526 | (−) | (+) | (−) | (+) | (−) |
| 12D110 | (−) | (+) | (−) | (+) | (−) |
| 1D1416 | (−) | (−) | (−) | (+) | (−) |
| 1D1565 | (−) | -) | (−) | (+) | (−)/(+) |

In the table, a minus symbol (−) indicates no growth detected, indicating the strain is sensitive to the antibiotic; a plus symbol (+) indicates well distributed colony's growth detected, indicating the strain is resistant to the antibiotic; and (−)/(+) indicates little growth (few colonies) at the antibiotic concentrations used. Table 3 shows that all of the 8 strains were sensitive to kanamycin at 100 mg/L and carbenicillin at 250 mg/L, but were resistant to ampicillin at 100 mg/L.

The frequency of citrus explant transformation using these eight *Agrobacterium* strains was determined. As seen on FIG. 4 white bars, according to initial data from first set of transformation DsRed transient expression, strain 1416 showed the highest frequency (67%) followed by EHA105 (63%), 159 (23%), 1526 (6%), and 1104 (3%). After two rounds on selection regeneration media (SRM), it was observed that some of the tissues transformed with strains 1416 and 159 had proliferated around the vascular cambium cells layer, and produced callus/tumors around these tissues. See for example, FIG. 5C which shows health tissue transformed with 1416, and FIG. 5D which shows proliferating tissues transformed with 1416. On the other hand, no tumors were observed formed from tissues transformed with EHA105, 1104 or 1526. See for example, FIG. 5A which shows healthy tissue transformed with EHA105, FIG. 5B which shows proliferating tissue transformed with EAH105, FIG. 5E which shows healthy tissue transformed with 1104, and FIG. 5F which shows bacterial overgrowth, and necrotic and dying tissues transformed with wildtype 1104. In addition, with time, DsRed expression disappeared from tissues transformed with 1104 and 1526. The frequency of tumor formation was higher from 1416 (36%) than from 159 (10%). Although gall size was larger from 1416 than from 159, the difference was not measured. As seen in FIG. 7A to FIG. 7D, tumors formed in CrZ epicotyls transformed with wildtype *Agrobacterium* strains 1416 and 159 presented stable DsRed expression. FIG. 7A presents an image of tumors formed when transformed with wildtype strain 1416; FIG. 7B presents an image of the DsRed expression in tissues transformed with wildtype strain 1416; FIG. 7C presents an image of tumors formed when transformed with wild type strain 159; FIG. 7D presents an image of the DsRed expression in tissues transformed with wildtype strain 159. Six to eight weeks later, DsRed expressing shoots were observed regenerating from only juvenile tissues transformed with strains EHA105 and 1416. The frequency of transgenic shoot regeneration was highest from EHA105 (21%) followed by 1416 (15%) (FIG. 12).

The data presented in this Example shows that of forty-five wild type *Agrobacterium* strains tested twenty-five grew in LB medium without antibiotics, and eight strains were capable of transient transformation of citrus tissue.

Example 3

Surfactant Effect

The effect of a surfactant on the transformation efficiency of the different *Agrobacterium* strains was determined.

Preliminary optimization experiments we performed testing different components in an attempt to enhance transformation frequency in citrus. These preliminary experiments showed that incorporating a surfactant in *Agrobacterium* inoculation media significantly increased transformation frequency when EHA105 was used in citrus. Therefore, in a second set of experiments, surfactant was added in the inoculation liquid media for the four wild type strains as well as EHA105. Data of the DsRed expression frequency obtained when transforming citrus tissue using different *Agrobacterium* strains in the absence of surfactant (bars with diagonal stripes) and in its presence (white bars) is shown in FIG. 4. This figure shows that DsRed expression frequency increased when *Agrobacterium* transformation with EHA105 and 1416 was performed in the presence of surfactant, while it decreased when *Agrobacterium* transformation with 159, 1526, or 1104 was performed in the presence of surfactant. DsRed expression frequency increased significantly in tissues transformed with 1416 (88%) and EHA105 (84%), while it decreased in tissues transformed with 159 (9%), 1526 (4%), or 1104 (2%). In addition to producing the highest frequency of DsRed expression in CrZ tissues, the combination of using 1416 strains with a surfactant showed higher transformation of vascular tissues including the layers of meristem cells in the cork cambium layer and the vascular cambium meristem cells when compared to the other strains, including EHA105. The effect of surfactant on gall formation frequency agreed with the pattern of DsRed frequency from the 4 strains. As seen in FIG. 12, it was observed that strain 1416 induced higher frequency of tumors (78%) followed by a lower frequency from strain 159 (6%). No galls were observed from strains 1526 and 1104. Interestingly, after 4 to 6 weeks in culture, the numerous galls formed from strain 1416 were 2-3 times larger in size (3-5 mm) than tumors formed from strain 159 (1-2 mm). Moreover, when surfactant was added these tumors from strain 1416 were larger than those formed from strain 1416 in the absence of surfactant (1-2 mm). The tumor sizes from strain 159 were not affected by the addition of surfactant, but they were less in frequency. As seen in FIG. 7A and FIG. 7C, when viewed under light microscopy, proliferated tumors from strains 1416 and 159 were a mix of white and greenbluish color. As seen in FIG. 7B and FIG. 7D, 80% to 90% of tumors from strains 1416 and 159 expressed DsRed under a fluorescence microscope.

Figure 8A:
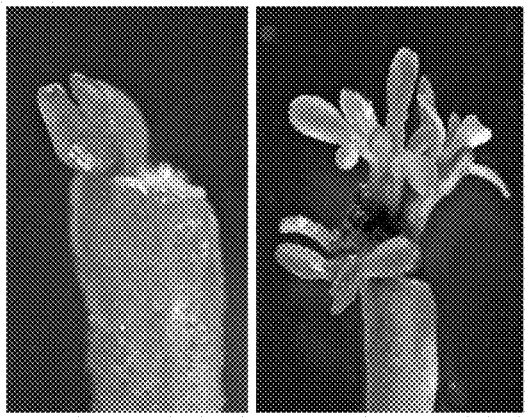
FIG. 8A to FIG. 8D depict images of shoots regenerated from CrZ epicotyls transformed with 1416/pCTAGV-KCN3.
Figure 8B:
Figure 8C:
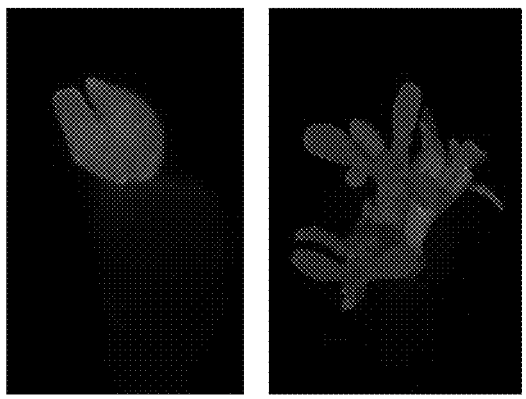
Figure 8D:
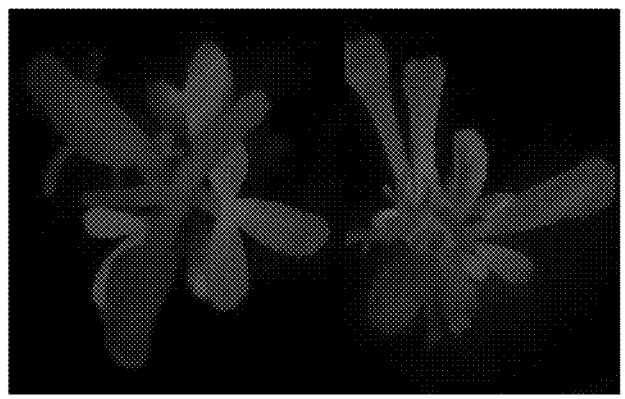
Figure 9A:
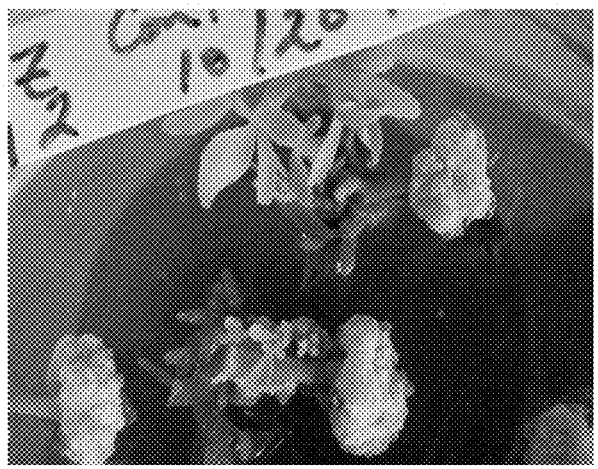
FIG. 9A to FIG. 9D depict close images of citrus shoot regenerated from non-transformed and transformed Carrizo epicotyl tissues.
Figure 9B:
Figure 9C:
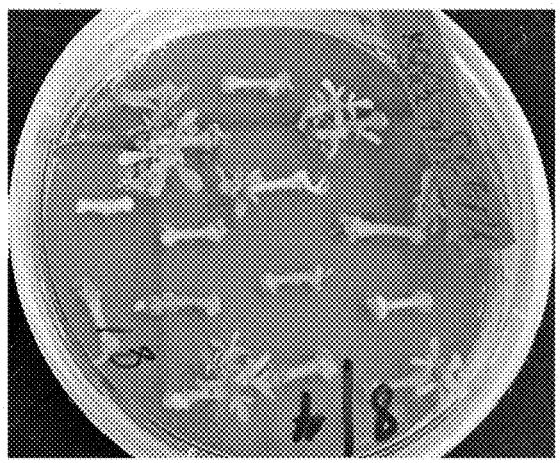
Figure 9D:
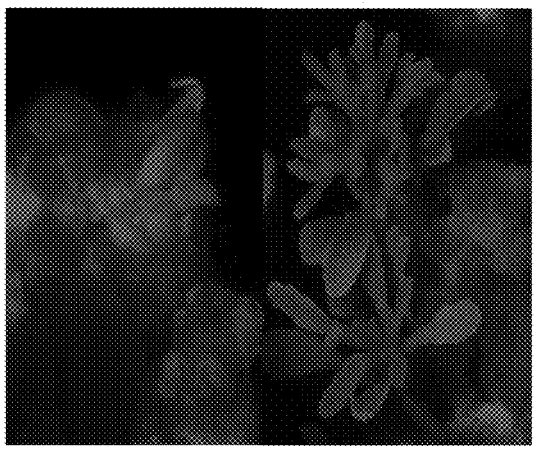
Figure 10:
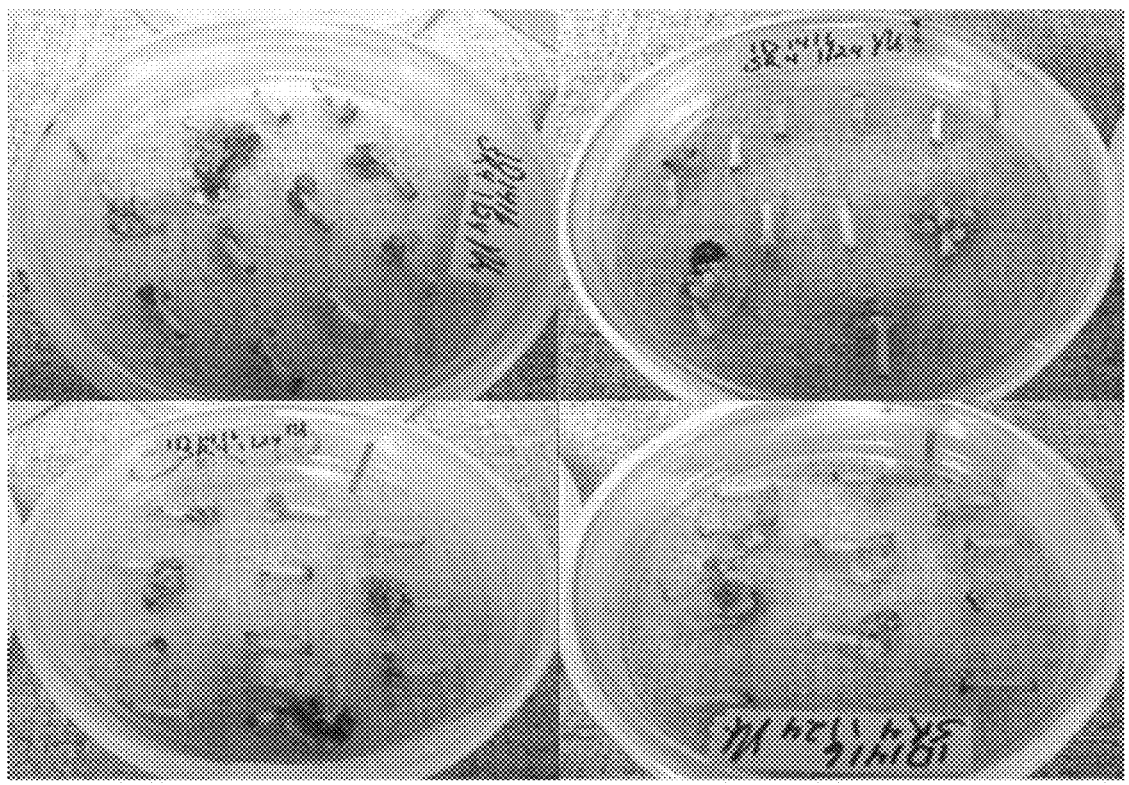
FIG. 10 depicts images of numerous galls formed in healthy looking, epicotyl explants transformed with 1416 strain.
Figure 11A:
FIG. 11A and FIG. 11B depict images of normal and healthy CrZ shoots regenerated from galls produced by strain 1416 and cultured on shoot maintenance medium.
Figure 11B:

As seen in FIG. 8A and FIG. 8B, gall tissues formed from strain 1416 continued to proliferate, and resembled the healthy morphology of the wild type, non-transformed CrZ epicotyls on regeneration media. Surprisingly, a number of morphologically-normal, and DsRed-expressing shoots were observed regenerating directly from transformed CrZ epicotyls through organogenesis and circumventing tumors. FIG. 8A and FIG. 8B depict images of normal and healthy CrZ shoots regenerated from galls produced by strain 1416 and cultured on shoot maintenance medium. As seen on FIG. 8C and FIG. 8D, these shoots were expressing a uniform DsRed expression, and continued to grow. Similarly, a high number of normal shoots regenerated from galls, and expressed DsRed. Only a low percentage of regenerated shoots from galls (10-13%) did not express DsRed. A few shoots were observed that were chimera to DsRed expression (6-8%). As seen on FIG. 12, the frequency of transgenic shoot regeneration was significantly increased from tissues transformed with EHA105 (32%) and 1416 (49%), and no shoots were regenerated from 159 and other strains. Since strain 1416 was highly efficient in transferring DsRed to citrus tissues and regenerating transgenic citrus shoots, transformation studies were focused on using this strain.

Figure 13A:
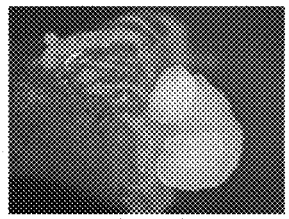
FIG. 13A to FIG. 13H depict images of tumor formation and stable DsRed expression in internodal segments from mature tissues transformed with wild type strain 1416.
Figure 13B:
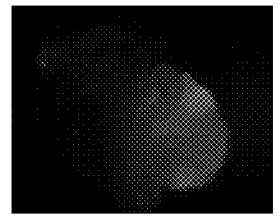
Figure 13:
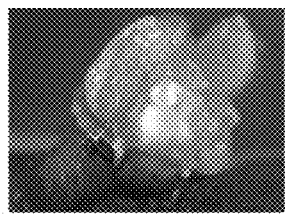
Figure 13D:
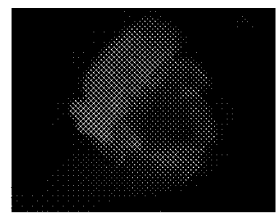
Figure 13E:
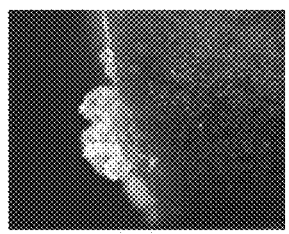
Figure 13F:
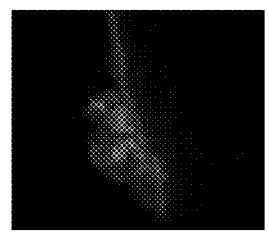
Figure 13G:
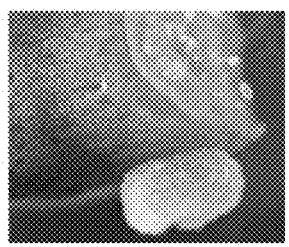
Figure 13H:
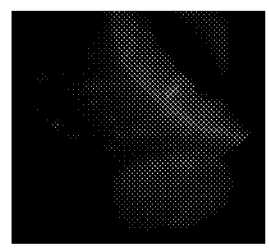
Figure 14A:
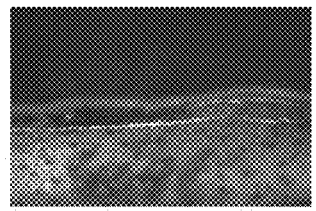
FIG. 14A to FIG. 14H depict images of tumor formation and stable DsRed expression in the cork cambium cell layer of internodal segments from mature tissues transformed with wild type strain 1416.
Figure 14B:
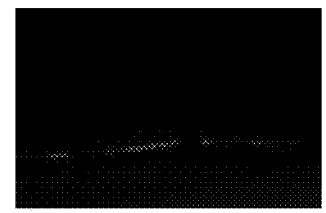
Figure 14C:
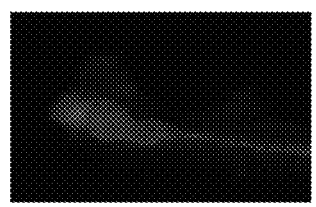
Figure 14D:
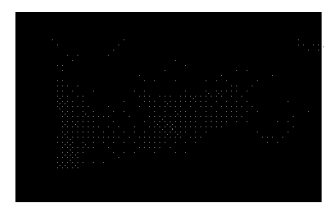
Figure 14E:
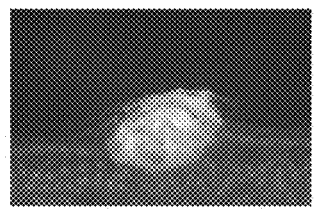
Figure 14F:
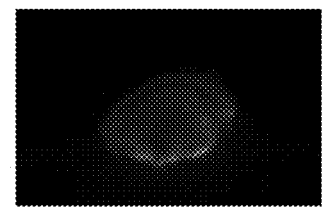
Figure 14G:
Figure 14H:
Figure 15:
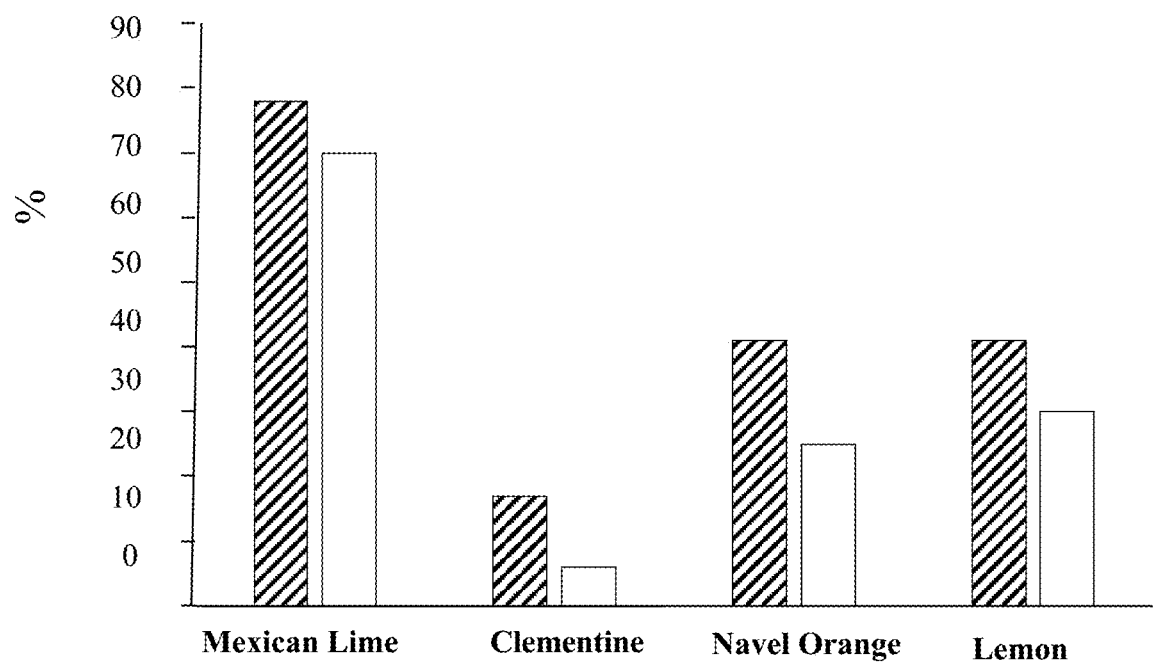
FIG. 15 depicts a graph of the average transformation efficiency and gall formation in mature citrus tissues from different varieties transformed with strain 1416. The Y axis shows the percentage galls or percentage of shoots regenerated expressing DsRed. The X axis presents the different citrus used. Bars with diagonal stripes indicate transgenic gall formation; white bars indicate gall expressing DsRed.
Figure 16A:
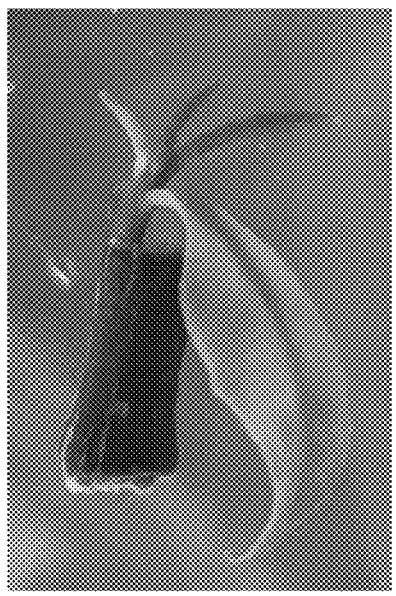
FIG. 16A to FIG. 16D depict images of citrus tissues transformed with *Agrobacterium* 1416.
Figure 16B:
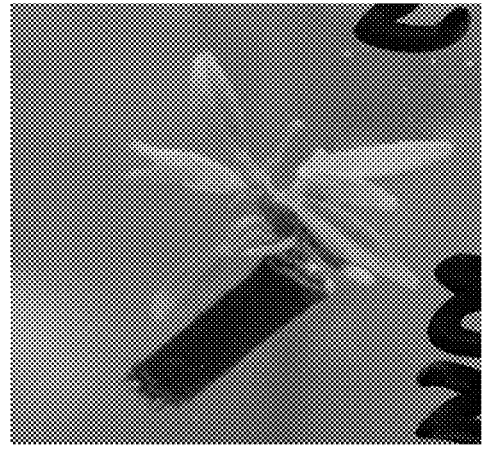
Figure 16C:
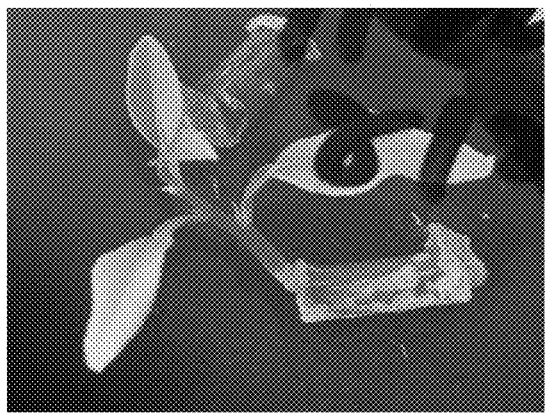
Figure 16D:
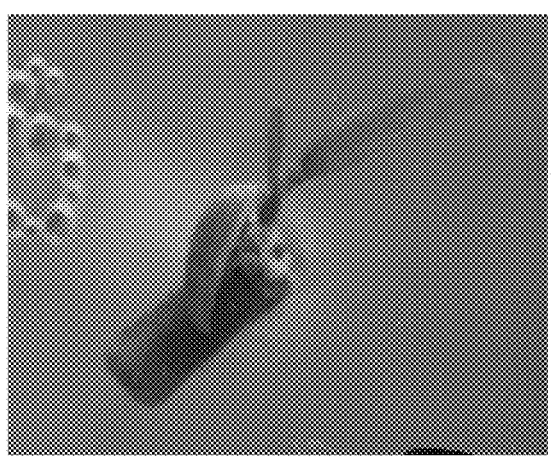

As seen in FIG. 13A to FIG. 13H, tissues transformed with strain 1416 competent citrus cells showed the lowest necrosis and detrimental responses to transformation and regeneration compared to other strains. As seen in FIG. 13A, after 10 to 15 days in culture, CrZ epicotyls formed tumors and continued to grow. All proliferated tumors were a mix of white and green-bluish color under light and expressed DsRed under a fluorescence microscope. Further, similar results were obtained from intermodal segments of mature tissues from Mexican lime, navel orange, clementine and lemon. Tumor formation in mature tissues was the highest in Mexican lime (71%) followed by Navel orange (45%), lemon (32%), and clementine (23%). Most of the tumors were expressing DsRed which indicates that 1416 transfers both T-DNA from pTi-1416 and binary vector pCTAGV-KCN3. With the novel efficient strain obtained in this study, DsRed foci were evenly distributed throughout the tissues. FIG. 13A to FIG. 13H depict images of tumor formation and stable DsRed expression in internodal segments from mature tissues transformed with wild type strain 1416. FIG. 13A shows an image of a sterilized mature transformed Mexican lime shoot; FIG. 13B shows an image of the stable DsRed expression in the sterilized mature transformed Mexican lime shoot; FIG. 13C shows an image of a sterilized mature transformed Naval orange; FIG. 13D shows an image of the stable DsRed expression in the sterilized mature transformed Naval orange; FIG. 13E shows an image of a sterilized mature transformed clementine; FIG. 13F shows an image of the stable DsRed expression in the sterilized mature transformed clementine; FIG. 13G shows an image of a sterilized mature transformed lemon; FIG. 13H shows an image of the stable DsRed expression in the sterilized mature transformed lemon. Further analysis of tissue-specific transformation in citrus revealed that the C58 strain also showed a preference for transformation of vascular tissue. For all other known and novel strains, no tissue specificity of transformation was observed with Carrizo epicotyl tissues.

The results obtained in this Example show that *Agrobacterium* 1416 efficiently transforms different types of citrus tissues.

Example 4

Identification of *Agrobacterium* Strains and Ti Plasmids

Using sequencing, the identity of the different *Agrobacterium* strains was determined.

Sequencing results of four wild type *Agrobacterium* strains revealed that two of the strains, 1104 and 1526, were possible of A. *Rhizobium* type. While strains 159 and 1416 were possible *A. tumefaciens*. Strain 159 is highly related to the nopaline C58 strain, and the pTi-159 is 98% similar to pTi-058 according to sequencing annotation results. Although strain 1416 initially showed resemblance to C58 and pTi-058, it may be of a nopaline type. Since strain 1416 was superior in citrus transformation, it was elected for further study and characterization. After detailed sequence analysis, 3000 bp DNA fragments containing the upstream and downstream DNA regions of the T-DNA right border region were found to be deleted and completely different from the pTi-058 and 159 nopaline strains. In addition, when compared to pTi-058 and pTi-159, approximately 1000 bp sequences are deleted inside the left border. Moreover, strain 1416 has two pAt plasmids, one which contains a second complete set of virB genes and the other contains third a partial set (7 out of 11) of virB genes.

To confirm sequencing results and better determine the type of plasmid in the four strains, PCR was performed using genomic DNA as templates with primers against seven known genes in the T-DNA region and outside of T-DNA region of the Ti plasmid. The sequences of the primers used are described in Table 1. Table 4, shown below, lists the genes amplified, their known source, and their expected size in base pairs (bp).

TABLE 4

GENES AMPLIFIED

| Gene Name | Source | Expected size (bp) |
|---|---|---|
| Neomycin phosphotransferase (NptII) | | 627 |
| C protein (CPro) | Wild type pTiI416 T-DNA (near left border) | 1581 |
| D-lysopine dehydrogenase/D-Octopine dehydrogenase (Lod) | Wild type pTiI416 T-DNA (near right border) | 1128 |
| Glycerophosphoryl diester phosphodiesterase (Gpdp) | pTiI416 (outside left border) | 1075 |
| Multi species NAD/NADP ocs/nos dehydrogenase (NNond) | pTiI416 (outside right border) | 1109 |
| Trans-zeatin synthesizing (Tzs) | pTi-Nopaline | 998 |
| Agrocinopine synthase (Acs) | Wild type plasmid T-DNA | 1071 |
| Nopaline synthase (Nos) | Wild type nopaline plasmid T-DNA | 1242 |

TABLE 4-continued

GENES AMPLIFIED

| Gene Name | Source | Expected size (bp) |
|---|---|---|
| Vir G | pTil416 and pTiC58 | 430 |
| Octopine synthase (Ocs) on wild type T-DNA | Wild type octopine plasmid T-DNA | 1077 |
| aminoglycoside phosphotransferase (Aph3) | | 765 |

Design of the primer sequences for the genes was based on consensus sequences of both the nopaline and octopine type Ti plasmid, as well as based on the inventors' sequence results (RF Barker, et al., 1983, "Nucleotide sequence of the T-DNA region from the *Agrobacterium tumefaciens* octopine Ti plasmid pTi15995," Plant Mol. Biol. 2: 335-350; B Goodner, et al., 2001, "Genome Sequence of the Plant Pathogen and Biotechnology Agent *Agrobacterium tumefaciens* C58," Science 294 (5550): 2323-2328; D W Wood, et al., 2001, "The Genome of the Natural Genetic Engineer *Agrobacterium tumefaciens* C58," Science 294 (5550): 2317-2323; M Cheng et al., 2004, "Invited Review: Factors influencing *Agrobacterium*-mediated transformation of monocotyledonous species," In Vitro Cell. Dev. Biol.—Plant 40: 31-45; H H Hwang et al., 2013, "Characterization and host range of five tumorigenic *Agrobacterium tumefaciens* strains and possible application in plant transient transformation assays," Plant Pat. 62: 1384-1397). The DNA fragments were amplified from six previously-characterized *A. Tumefaciens* strains (A208, A348, C58, Ach5, NT1RE (pJK270) and 1D1609). Since strains 1104 and 1526 were considered *Rhizobium*, and strains 159 and 1416 were considered *Tumefaciens*, it was predicted that both strains 159 and 1416 contained the Ti plasmids. To determine opine type of Ti plasmid in these strains, genomic DNA PCR was performed with primers detecting the genes listed in Table 4, agrocinopine synthase (acs), nopaline synthase (nos) or octopine synthase (ocs) and octopine synthase (ocs1416) in the T-DNA region. PCR results confirmed the presence of ocs1416 gene in the T-DNA region, upstream of the right border region, but not the ocs gene of the octopine-type Ti plasmid (RF Barker, supra). With the ocs1416 primers, a 1071 bp DNA fragment was amplified from only the 1416 strain Ti plasmids. Further analysis showed that the ocs1416 gene sequence induces a lysopine dehydrogenase enzyme matching, the known octopine synthase gene. The acs and nos genes both locate in the T-DNA region of the nopaline-type Ti plasmid (B Goodner, et al., 2001, "Genome Sequence of the Plant Pathogen and Biotechnology Agent *Agrobacterium tumefaciens* C58," Science 294 (5550): 2323-2328; D W Wood, et al., 2001, "The Genome of the Natural Genetic Engineer *Agrobacterium tumefaciens* C58," Science 294 (5550): 2317-2323). Since strain 159 of the C58 and the Ti plasmid is also the same as pTiC58, it was utilized as a positive control for the nopaline type. The acs primers amplified a 1071 bp DNA fragment from 159 and, surprisingly, also from 1416 *A. tumefaciens* strains. Additionally, a 1242 bp DNA fragment was only amplified from 159 *A. tumefaciens* strain and not from the 1416 strain. Since the design of the nos primers was based on the conserved region of the nos gene in the nopaline-type Ti plasmids pTiC58 (accession no. AJ237588), pTiSAKURA (accession no. AB016260), this eliminated the nopaline type from strain 1416. However, according to the sequence results, DNA sequences outside T-DNA and near the right border were considered as a noplaine synthase gene related to the pTiC58 nopaline synthase gene family. Using nos 1416 primers, a 1071 bp DNA fragment was amplified from only the 1416 strain Ti plasmid, but not from any of the other strains tested. PCR results confirmed the major differences in the sequences between the C58 nos gene and the 1416 nos gene. Because the trans-zeatin synthesizing (tzs) gene exists only in nopaline-type Ti plasmids (D E Akiyoshi, et al., 1985, "Cloning and nucleotide sequence of the tzs gene from *Agrobacterium tumefaciens* strain T37," Nucleic Acids Res. 13: 2773-2788; J S Beaty, et al., 1986, "Tzs, a nopaline Ti plasmid gene from *Agrobacterium tumefaciens* associated with trans-zeatin biosynthesis," Mol. Gen. Genet. 203: 274-280; G K Powell, et al., 1988, "Inducible expression of cytokinin biosynthesis in *Agrobacterium tumefaciens* by plant phenolics," Mol. Plant Microbe Interact. 1: 235-242), genomic DNA PCR was performed with the tzs gene primers. A 998 bp DNA fragment was amplified from strain 159, a nopaline *A. tumefaciens* strain, and interestingly from strain 1416. Hwang (Supra) reported that tzs was amplified from C58, NT1RE (pJK270) and A208, and shares homology with other prokaryotes such as *Pseudomonas savastanoi* and *Xanthomonas oryzae* but not from the three previously characterized *A. tumefaciens* strains A348, Achy and 1D1609, which contain octopine-type Ti plasmids.

Thus, PCR results with the nopine synthase and tzs genes made it difficult to confirm the type of Ti plasmid in strain 1416. This strain appears to be unique in having an octopine gene in the T-DNA, and nopaline synthase, tzs, VirG of C58 outside the T-DNA. The results shown here clearly have proven that this strain is a novel strain and the inventors have called it "Octopine hybrid like nopaline." Confirming these results, the 3000 bp DNA fragments containing the upstream and downstream DNA regions of the T-DNA right border region appeared completely different from the pTiC58 and 159 nopaline strains. In addition, when compared to pTiC58 and 159, there were approximately 1000 bp of deleted sequences inside the left border. Moreover, strain 1416 has a second pAt plasmid, (pAt2), which sequence analysis related it to a *Rhizobium*-type of plasmid. Amplified DNA fragments were cloned into the pBluescript SK+ for DNA sequence analysis. The DNA sequences of these amplified products were deposited in GenBank (accession nos. JX901130 to JX901137). The resulting sequences of the 1700 bp DNA fragments containing the right border and the nos gene (JX901131, JX901132, JX901135 and JX901137) from the four *A. tumefaciens* strains completely matched the corresponding regions of pTiC58. Despite no amplification with the nos gene primer set and the bacterial 1D1108 strain (FIG. 1), the DNA sequences of the 1700 bp DNA fragment (JX901131) from the same bacterial strain confirmed the existence of the nos gene near the right border region of 1D1108 Ti plasmid. Similarly, the 1700 bp DNA fragment containing the left border and the acs gene (JX901130, JX901133, JX901134 and JX901136) from the four *A. tumefaciens* strains were highly homologous with pTiC58 (99%), with only a 1 to 3 nucleotide mismatch. The 25 bp T-DNA left and right border sequences from the four strains 1D1108 (JX901130, JX901131), 1D1460 (JX901132, JX901133), 1D1478 (JX901134, JX901135) and 1D1487 (JX901136, JX901137), were identical to the nopaline-type Ti plasmids pTiC58 (AJ237588), pTiSAKURA (AB016260), and pTiT37 (J01826, J01825). This suggests that strains 1D1108, 1D1460, 1D1478, and 1D1487 contain typical nopaline-type Ti plasmids. PCR results with the acs and tzs genes (FIG. 1) suggested that the nopaline-type Ti plasmid may exist in the A. Tumefaciens strain 1D132. The DNA sequences and gene locations in the right and left ends of T-DNA regions in the ID132 strain might not completely match the corresponding region of previously characterized nopaline-type Ti plasmids, and may therefore affect genomic DNA PCR amplification of the 1D132 strain with primers against T-DNA border regions.

The results obtained in this Example show that 1416 is a novel *Agrobacterium* strain that efficiently transforms citrus tissues.

Example 5

*A. tumefaciens* Strain 1416 Disarmed Strains

Four different disarmed strains of 1416 were prepared, 1416G, 1416G-NBR3, 1416Gr, and 1416Gt.

The map in FIG. 19 depicts of a portion of 1416G-NRB3, a disarmed strain derived from *Agrobacterium* strain 1416, and comprising the 1416 LB HR Arm containing 1075 bp of genome homology sequence used for precise genome targeting of the GANNTRY technology; the 238 bp LB flank (C58) and 25 bp LB T-DNA repeat region obtained from the naïve C58 genome and required for T-DNA transfer. More specifically, the 25 bp LB T-DNA repeat region in required and the 238 bp LB flank (C58) may enhance the fidelity of T-DNA transfer; the 145 bp Tomato pectinase TermA2 is a tomato terminator added to provide transcriptional insulation from the surrounding genome on the T-DNA/GAANTRY assembly domain); a 55 bp attB(TP901) site (TP901 attB); a 789 bp Gentamicin 3 acetyltransferase gene (aacC1) that provides gentamicin resistance to microbes; 106 bp res(ParA) site (ParA resolution site); the 1416 RB HR Arm containing 1110 bp of genome homology sequence used for precise genome targeting of the GAANTRY technology. This strain was designed to be used with either binary vector (kanamycin or spectinomycin based selection) transformation or GAANTRY T-DNA stacking technology and transformation.

The 1416Gr strain is a recA knockout strain, and 1416Gt is a Thymidylate Synthase gene knockout strain. Both of these strains are derived from 1416G. The lines were prepared following the CRISPR editing protocol described by SD Rodrigues, et al. (2020, "Efficient CRISPR-mediated base editing in *Agrobacterium* spp," Proc. Natl. Acad. Sci. U.S.A. 118(2): e2013338118).

Example 6

Generation of Symbionts

The *Agrobacterium* strains described herein (1416, 1416G, 1416G-NBR3, 1416Gr, and 1416Gt) may be used in at least two different methods to generate symbionts or symbiont-forming inoculum.

One such method for generating symbionts or symbiont-forming inocula is the co-inoculation of a disarmed *Agrobacterium* spp. strain with a wild-type *Agrobacterium* spp. strain. The wild-type *Agrobacterium* spp. strain may be 1416, and the disarmed *Agrobacterium* spp. strain may be 1416G, 1416G-NBR3, or 1416Gr. The disarmed *Agrobacterium* spp. strain is used to express a polynucleotide of interest, and the wild-type *Agrobacterium* spp. strain is used to transfer phytohormone genes to the plants. A disarmed *Agrobacterium* strain (such as 1416G, 1416G-NBR3, 1416Gr, or 1416Gt) carrying a polynucleotide of interest and the wild-type 1416 strain may be grown using procedures common in the art, Each strain is then centrifuged to recover a bacterial pellet, which is then resuspended in inoculation buffer (10 mM $MgCl_2$, 10 mM MES pH 5.6, 100 µM acetosyringone. The disarmed strain may be resuspended to an $OD_{600}$ of 1, and the wild-type strain may be resuspended to an $OD_{600}$ of 0.1. The resuspended strains were kept at room temperature for 1 to 3 hours and mixed together before inoculation of the plant tissue. Symbiont forming inoculum or symbiont are then formed.

Another method for generating symbionts or symbiont-forming inocula uses a single *Agrobacterium* spp, to inoculate a plant or plant cell. To use this method, any one of the 1416 disarmed *Agrobacterium* spp. strains (1416G, 1416G-NBR3, or 1416Gr) carrying a binary vector comprising both, a polynucleotide of interest and a phytohormone gene polynucleotide may be used to inoculate plant cells. The binary vector contains a cassette of approximately 7.5 Kb plant growth regulators, (indole-3-acetamide hydrolase, tryptophan 2-monooxygenase, isopentenyl transferase, indole-3-lactate synthase) and a polynucleotide of interest operably linked to a constitutive or inducible promoter. As stated above, the pCTAGV-KCN3 plasmid also contains a selectable marker gene (kanamycin) to allow for selection of cells carrying the pCTAGV-KCN3 plasmid. Plant tissue is inoculated with a suspension of the pCTAGV-KCN3-containing *Agrobacterium* spp. to form a symbiont or a symbiont-forming inoculum.

Once the DNA is delivered into the host plant cell genome, the expression of the phytohormones will induce and stimulate plant tissues to grow a mixed cultured symbiont having a collection of cells with different gene insertions and expression levels of polynucleotide of interest and the phytohormones. The mixed culture symbiont can grow autonomously and connect to the host plant via vascularization by connecting with one or both of the phloem and xylem where the polynucleotide of interest product may be transported to the host plant. For dispersion throughout the host plant, the polynucleotide of interest product produced by the symbiont may be transferred via the apoplast and/or the symplast and/or through the phloem and or xylem.

The mixed culture symbiont can subsequently be excised and grown in hormone-free culture where cells having desirable traits and expression level can be selected, allowing for isolation of uniform symbiont-forming inoculum(s). Selection for pure-culture symbiont-forming inoculum(s) may include the use of antibiotic selection, serial dilution/division of the culture, or may be converted to a protoplast, and single protoplast cells can be isolated and grown up to a pure culture. Symbiont-forming inoculum(s) can be selected for those expressing desirable attributes in addition to the expression of the polynucleotide of interest and the introduced phytohormone(s). In addition, the use of antibiotics can also be used to eliminate *Agrobacterium* from the mixed cultured symbiont-forming inoculum.

Selected symbiont-forming inoculum(s) are transplanted onto a host plant where they can attach and provide the polynucleotide of interest expression product or a product of the polynucleotide of interest expression product for dispersion into and/or throughout the plant. The polynucleotide of interest expression product can be an enzyme that is involved in the biosynthesis of a product in the symbiont, and it is the product that is transported out of the symbiont and into the host plant. Once at least one symbiont-forming inoculum is attached to the plant host it forms what is termed "symbiont"

We claim:

1. A disarmed *Agrobacterium* strain 1416G having ATCC deposit No. PTA-127288, or a derivative thereof.

2. A derivative of the disarmed *Agrobacterium* strain of claim 1, wherein the *Agrobacterium* strain comprises a 145 bp non-coding terminator sequence for tomato pectinase.

3. The disarmed *Agrobacterium* strain of claim 2, wherein the *Agrobacterium* strain comprises a 55 bp attB site and a 789 bp Gentamicin 3 acetyltransferase gene.

4. The disarmed *Agrobacterium* strain of claim 1, wherein the *Agrobacterium* strain comprises a 795 bp aminoglycoside phosphotransferase gene.

5. The disarmed *Agrobacterium* strain of claim 4, wherein the *Agrobacterium* strain comprises a 52 bp A118 phage attachment site.

6. The disarmed *Agrobacterium* strain of claim 1, wherein the *Agrobacterium* strain comprises a 106 bp ParA resolution site.

7. The disarmed *Agrobacterium* strain of claim 1, wherein the disarmed *Agrobacterium* strain is *Agrobacterium* strain 1416G, 1416G-NRB3, 1416Gr, or 1416Gt.

8. A method for producing a transgenic plant, fungal, or algae cell having a polynucleotide of interest, the method comprising contacting a plant, fungal, or algae cell with a culture comprising a disarmed *Agrobacterium* strain of claim 1 having the polynucleotide of interest, and incubating the plant, fungal, or algae cell in contact with the disarmed *Agrobacterium* strain having the polynucleotide of interest in selection regeneration media at a proper temperature and for a sufficient amount of time to allow for the formation of a transgenic plant, fungal, or algae cell.

9. The method of claim 8, wherein the plant cell is from a plant or part thereof.

10. The method of claim 9, wherein the plant or part thereof is a citrus plant or part thereof.

11. The method of claim 10, wherein the citrus plant or part thereof is a seedling or a mature shoot.

12. The method of claim 10, wherein the citrus plant or part thereof is from a lime, a lemon, an orange, a citron, or a grapefruit.

13. The method of claim 8, wherein the disarmed *Agrobacterium* strain is *Agrobacterium* strain 1416G, 1416G-NRB3, 1416Gt, or 1416Gr.

14. A kit comprising a disarmed *Agrobacterium* strain of claim 1.

15. A kit comprising a disarmed *Agrobacterium* strain of claim 7.

16. A symbiont or symbiont-forming inoculum comprising *Agrobacterium* strain 1416 and any one of disarmed *Agrobacterium* strains 1416G, 1416G-NRB3, 1416Gr, or 1416G carrying a polynucleotide of interest; or comprising a disarmed *Agrobacterium* strain 1416G, 1416G-NRB3, 1416Gr, or 1416Gt carrying any synthetic transfer DNA comprising a polynucleotide of interest and a phytohormone gene polynucleotide.

17. The disarmed *Agrobacterium* strain of claim 1, wherein the *Agrobacterium* strain comprises a recA gene knockout.

18. The disarmed *Agrobacterium* strain of claim 1, wherein the *Agrobacterium* strain comprises a thymidylate synthase gene knockout.

* * * * *